United States Patent
Vicary et al.

(10) Patent No.: US 7,632,490 B2
(45) Date of Patent: Dec. 15, 2009

(54) USE OF IL-1 ANTAGONISTS TO TREAT GOUT

(75) Inventors: Catherine Vicary, New York, NY (US); Scott Mellis, New Rochelle, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/200,681

(22) Filed: Aug. 28, 2008

(65) Prior Publication Data

US 2009/0123446 A1    May 14, 2009

Related U.S. Application Data

(63) Continuation-in-part of application No. 11/975,593, filed on Oct. 19, 2007.

(60) Provisional application No. 60/853,385, filed on Oct. 20, 2006.

(51) Int. Cl.
*A61K 38/03* (2006.01)
*A61K 38/19* (2006.01)
*A61K 38/44* (2006.01)
*A61K 31/195* (2006.01)

(52) U.S. Cl. .................. 424/85.1; 424/94.4; 514/2; 514/404; 514/469

(58) Field of Classification Search ............... None
See application file for complete search history.

(56) References Cited

U.S. PATENT DOCUMENTS

| | | | |
|---|---|---|---|
| 6,472,179 B2 | 10/2002 | Stahl et al. | |
| 6,927,044 B2 | 8/2005 | Stahl et al. | |
| 2005/0129685 A1 | 6/2005 | Cao et al. | |
| 2005/0197293 A1* | 9/2005 | Mellis et al. | ............ 514/12 |
| 2007/0161559 A1 | 7/2007 | Petrilli et al. | |

FOREIGN PATENT DOCUMENTS

| WO | WO 2004/100987 A1 | 11/2004 |
|---|---|---|
| WO | WI 2005/117945 A1 | 12/2005 |
| WO | WO 2006/084145 A1 | 8/2006 |
| WO | WO 07/077261 A1 | 7/2007 |
| WO | WO 2007/077042 A1 | 7/2007 |

OTHER PUBLICATIONS

Hashizume et al. Advances in Experimental medicine and Biology, 1989, vol. 253a, pp. 219-224.*
Takahashi et al, Annals of The Rheumatic Diseases, 2003, vol. 62, pp. 572-575.*
Naomi Schlesinger, Drugs; 2004, vol. 64 Issue 21, p. 2399-2416.*
Martinon, F. 2006. Gout-associated uric acid crystals activate the NALP3 inflammasome. Nature 440(7081): 237-241.
Gabay, C. 2003. IL-1 Trap. Current Opinion in Investigational Drugs 4(5): 593-597.

* cited by examiner

*Primary Examiner*—Christine J Saoud
*Assistant Examiner*—Fozia M Hamud
(74) *Attorney, Agent, or Firm*—Valeta Gregg; Frank R. Cottingham

(57) ABSTRACT

Methods of treating, inhibiting, or ameliorating gout, including chronic acute (refractory) gout, pseudogout, or drug-induced gout, in a human subject in need thereof, comprising administering to a subject in need a therapeutic amount of an interleukin 1 (IL-1) antagonist, wherein the incidence of a gout flare is reduced or inhibited.

17 Claims, No Drawings

USE OF IL-1 ANTAGONISTS TO TREAT GOUT

CROSS-REFERENCE TO RELATED APPLICATIONS

This application is a continuation-in-part of U.S. patent application Ser. No. 11/975,593 filed 19 Oct. 2007, which claims the benefit under 35 USC § 119(e) of U.S. Provisional 60/853,385 filed 20 Oct. 2006, which applications are herein specifically incorporated by reference in their entireties.

BACKGROUND

1. Field of the Invention

The invention relates to methods of using interleukin-1 (IL-1) antagonists to treat metabolic rheumatic disorders associated with hyperuricemia, including gout, and chronic active (refractory) gout. Further, the invention encompasses treatment of conditions such as pseudogout and drug-induced gout.

2. Description of Related Art

Metabolic rheumatic disorders associated with hyperuricemia, such as gout, are characterized by perversion of the purine metabolism resulting in hyperuricemia, i.e. an excess of uric acid in the blood, attacks of acute arthritis, and formation of chalky deposits in the cartilages of the joints. These deposits are made up chiefly of urates, or uric acid.

Known methods for treating gout include the use of uric acid synthesis inhibitors to inhibit the accumulation of uric acid in the body, and use of uric acid excretion promoters to accelerate the rapid excretion of uric acid accumulated in the body. Allopurinol is an example of a uric acid synthesis inhibitor. Probenecid, sulfinpyrazone and benzbromarone are examples of uric acid excretion promoters. Interleukin-6 (IL-6) has been proposed for use in the treatment of gout as a serum uric acid decreasing agent (see U.S. Pat. No. 6,007,804).

Pseudogout is not a hyperuremic disorder, and involves the deposition of calcium pyrophosphate.

BRIEF SUMMARY OF THE INVENTION

In a first aspect, the invention features a method of treating, inhibiting, or ameliorating metabolic rheumatic disorders associated with hyperuricemia comprising administering to a subject in need an interleukin 1 (IL-1) antagonist to a subject in need thereof. An IL-1 antagonist is a compound capable of blocking or inhibiting the biological action of IL-1, including fusion proteins capable of trapping IL-1, such as an IL-1 "trap". In a preferred embodiment, the IL-1 trap is an IL-1-specific fusion protein comprising two IL-1 receptor components and a multimerizing component, for example, an IL-1 trap described in U.S. Pat. No. 6,927,044, herein specifically incorporated by reference in its entirety. An IL-1 trap fusion protein comprises an IL-1 binding portion of the extracellular domain of human IL-1RAcP, an IL-1 binding portion of the extracellular domain of human IL-1RI, and a multimerizing component. In a specific embodiment, the IL-1 trap is the fusion protein shown in SEQ ID NO:10 (rilonacept) or a protein having at least 95% identity to the protein of SEQ ID NO: 10 and capable of binding and inhibiting IL-1. Use of the IL-1 trap to treat gout offers unexpected advantages relative to the use of prior art IL-1 antagonists for several reasons, including allowing alleviation of gout symptoms with reduced frequency of administration, reduced side effects such as, for example, reduced injection site inflammation or reduced immunogenicity.

In a preferred embodiment, the metabolic rheumatic disorder associated with hyperuricemia is gout. The subject being treated is most preferably a human diagnosed as suffering from gout, for example, chronic acute gout. The method of the invention encompasses preventing or ameliorating gout or hyperuricemia in a human subject suffering therefrom.

In a more specific embodiment, the gout condition being treated is drug-induced gout flares, including flares induced by xanthine oxidase inhibitors such as allopurinol and febuxostat; flares induced by urate oxidase, for example, uricase, rasburicase and pegylated uricase; and flares induced by uricosuric agents, such as probenecid, sulfinpyrazone, benzbromarone, and fenofibrate.

In one example of drug-induced gout, patients treated with a xanthine oxidase inhibitor, a urate oxidase, or a uricosuric agent, are treated with an IL-1 antagonist to reduce the frequency and severity of acute gout flares associated with the initiation of the xanthine oxidase inhibitor, a urate oxidase, or a uricosuric agent therapy. In a specific embodiment, the IL-1 antagonist reduces, inhibits or prevents the occurrence of drug-induced flares by at least about 50%, more preferably 60%, 75% or 80%, relative to not receiving the IL-1 antagonist; in even more specific embodiments, the IL-1 antagonist reduces, inhibits or prevents drug-induced gout flares by about 80% relative to not receiving the IL-1 antagonist. In a specific embodiment, the drug-induced gout flare is associated with initiation of allupurinol or febuxostat therapy.

In a second aspect, the invention features a method of treating, inhibiting, or ameliorating pseudogout, comprising administering to a subject in need an interleukin 1 (IL-1) antagonist to a subject in need thereof.

The methods of the invention includes administration of the IL-1 antagonist by any means known to the art, for example, subcutaneous, intramuscular, intravenous, transdermal administration or oral routes of administration. Preferably, administration is by subcutaneous or intravenous injection or intravenous infusion.

In specific embodiments of the therapeutic method of the invention, the subject is treated with a combination of an IL-1 trap and a second therapeutic agent. The second therapeutic agent an additional IL-1 antagonist and/or co-therapies such as uric acid synthesis inhibitors to inhibit the accumulation of uric acid in the body, for example, allopurinol, uric acid excretion promoters to accelerate the rapid excretion of uric acid accumulated in the body, for example, probenecid, sulfinpyrazone and/or benzbromarone are examples of uric acid excretion promoters; corticosteroids; non-steroidal anti-inflammatory drugs (NSAIDs); and/or cholchicine. Administration of the first and second therapeutic agents may be separately, simultaneously, or sequentially.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Metabolic Rheumatic Disorders Associated with Hyperuricemia

Gout is a group of metabolic rheumatic disorders associated with hyperuricemia and is the most common cause of an inflammatory arthropathy in middle-aged men. Gout is essentially a disorder of urate metabolism. Deposition of urate crystals in hyperuricemic individuals results in acute gout, characterized by agonizing pain and inflammation of rapid onset, most frequently affecting the first metatarsophalangeal joint. Hyperuricemia is associated with an increased risk of developing gout and this increases with the degree and duration of the hyperuricemia.

Treatment of gout aims to relieve pain and inflammation of the acute attack, and reduce the incidence of recurrent attacks. Dietary and pharmacological urate-lowering therapies principally aim to prevent clinical joint damage. Common approaches to the treatment of acute gout are corticosteroids, non-steroidal anti-inflammatory drugs (NSAIDs), and colchicine. The side effects of these drugs, particularly in the frail, elderly population who experience the highest incidence of acute gout, can be serious. An approach to the prevention of recurrent gout is the use of a xanthine oxidase inhibitor, allopurinol. However, allopurinol can have serious side effects such as allopurinol hypersensitivity syndrome (see, for example, Arellano et al. (1993) Ann Pharmacother 27:337-343).

Alternative drugs for preventing gout include the uricosuric agent sulphinpyrazone, limited by its side-effect profile, and benzbromarone and probenecid. Fenofibrate, a drug well known in the treatment of various forms of hyperlipidemia, has been proposed for the treatment of hyperuricemia.

Pseudogout

Pseudogout is a type of arthritis that, as the name implies, can cause symptoms similar to gout, but in reaction to a different type of crystal deposit. Pseudogout, sometimes referred to as calcium pyrophosphate deposition disease, can cause severe episodes of localized pain and swelling resulting in incapacitation for days or weeks. It also can cause more chronic arthritis that mimics osteoarthritis or rheumatoid arthritis. Knees are most often involved but wrists, shoulders, ankles, elbows or hands can be affected. Pseudogout is caused when deposits of calcium pyrophosphate crystals accumulate in a joint.

IL-1 Trap Antagonists

Interleukin-1 (IL-1) traps are multimers of fusion proteins containing IL-1 receptor components and a multimerizing component capable of interacting with the multimerizing component present in another fusion protein to form a higher order structure, such as a dimer. Cytokine traps are a novel extension of the receptor-Fc fusion concept in that they include two distinct receptor components that bind a single cytokine, resulting in the generation of antagonists with dramatically increased affinity over that offered by single component reagents. In fact, the cytokine traps that are described herein are among the most potent cytokine blockers ever described. Briefly, the cytokine traps called IL-1 traps are comprised of the extracellular domain of human IL-1R Type I (IL-1RI) or Type II (IL-1RII) followed by the extracellular domain of human IL-1 Accessory protein (IL-1AcP), followed by a multimerizing component. In a preferred embodiment, the multimerizing component is an immunoglobulin-derived domain, such as, for example, the Fc region of human IgG, including part of the hinge region, the CH2 and CH3 domains. An immunoglobulin-derived domain may be selected from any of the major classes of immunoglobulins, including IgA, IgD, IgE, IgG and IgM, and any subclass or isotype, e.g. IgG1, IgG2, IgG3 and IgG4; IgA-1 and IgA-2. Alternatively, the IL-1 traps are comprised of the extracellular domain of human IL-1AcP, followed by the extracellular domain of human IL-1RI or IL-1RII, followed by a multimerizing component. For a more detailed description of the IL-1 traps, see WO 00/18932, which publication is herein specifically incorporated by reference in its entirety. Preferred IL-1 traps have the amino acid sequence shown in SEQ ID NOs: 2, 4, 6, 8, 10, 12, 14, 16, 18, 20, 22, 24, and 26, or a substantially identical protein at least 95% identity to a sequence of SEQ ID NO:2, 4, 6, 8, 10, 12, 14, 16, 18, 20, 22, 24, or 26, and capable of binding and inhibiting IL1. Most preferably, the IL-1 antagonist is the protein of SEQ ID NO:10 (rilonacept).

In specific embodiments, the IL-1 antagonist comprises an antibody fragment capable of binding IL-1α, IL-1β, IL-1R1 and/or IL-1RAcp, or a fragment thereof. The preferred embodiment would be an antagonist of IL-1β. One embodiment of an IL-1 antagonist comprising one or more antibody fragments, for example, single chain Fv (scFv), is described in U.S. Pat. No. 6,472,179, which publication is herein specifically incorporated by reference in its entirety. In all of the IL-1 antagonist embodiments comprising one or more antibody-derived components specific for IL-1 or an IL-1 receptor, the components may be arranged in a variety of configurations, e.g., a IL-1 receptor component(s)-scFv(s)-multimerizing component; IL-1 receptor component(s)-multimerizing component-scFv(s); scFv(s)-IL-1 receptor component(s)-multimerizing component, ScFv-ScFv-Fc, etc., so long as the molecule or multimer is capable of inhibiting the biological activity of IL-1.

Treatment Population

The method of the instant invention provides treatment of pseudogout and metabolic rheumatic disorders associated with hyperuricemia to human patients suffering therefrom. The treatment population is thus human subjects diagnosed as suffering from pseudogout, gout or hyperuricemia. The invention encompasses the treatment of a human subject at risk of suffering from a recurrent gout episode or for developing gout or pseudogout.

The invention also encompasses treating a population of patients with drug-induced gout flares, including flares induced by gout therapeutics such as xanthine oxidase inhibitors, such as allopurinol and febuxostat; flares induced by urate oxidase, for example, uricase, rasburicase and pegylated uricase; and flares induced by uricosuric agents, such as probenecid, sulfinpyrazone, benzbromarone, and fenofibrate. By "drug-induced" gout flare is meant occurrence of or increased incidence of a gout flare associated with initiation of therapy to treat gout and/or administration of a therapeutic agent for the treatment of gout, for example, initiation of therapy with a xanthine oxidase inhibitor, urate oxidase, or a uricosuric agent. A gout flare is "associated" with initiation of gout therapy when the flare occurs contemporaneously or following at least a first administration of a therapeutic agent for the treatment of gout.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects).

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, commercial skin substitutes or angioplasty balloons or stents.

An initial dose may be followed by subsequent doses at a frequency of daily, weekly, biweekly, monthly or even less frequently. An initial dose, preferably administered subcutaneously or intravenously, may range from about 80 mg to about 500 mg of IL-1 antagonist, and subsequent doses may range from about 40 mg to about 250 mg of IL-1 antagonist.

Combination Therapies

In numerous embodiments, the IL-1 antagonists of the present invention may be administered in combination with one or more additional compounds or therapies. Combination therapy may be simultaneous or sequential. The IL-1 traps of the invention may be combined with, for example, TNF-inhibiting agents such as etanercept (ENBREL®, Amgen), infliximab (REMICADE®, Centocor), HUMIRA® (Abbott). Combination therapy may also include treatment with drugs currently used for the treatment or prevention of gout, including corticosteroids, non-steroidal anti-inflammatory drugs (NSAIDs); colchicine; xanthine oxidase inhibitors such as allopurinol and febuxostat; uricosuric agents such as sulphinpyrazone, benzbromarone and probenecid; and fenofibrate; and urate oxidase inhibitors such as uricase, rasburicase and pegylated uricase. Preferred co-therapeutics include NSAIDs, steroids and/or cholchicine.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention which will be effective in the treatment of delayed-type hypersensitivity can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

A Phase I/II, Placebo Controlled Pilot Study of the Safety, Tolerability, and Clinical Activity of Rilonacept for the Treatment of Chronic Active Gout Gout is a common disease with increasing incidence. There are approximately 5 MM Americans with gout. Medical needs are not fully met; a large number of individuals are either intolerant or not good candidates for current therapeutic or prophylactic strategies. This study explores the activity of rilonacept at one end of the gout spectrum: chronic active (refractory) gout. Results from this study may or may not be indicative of rilonacept's potential utility in acute active gout or in the prevention of gout flares; however, activity in this situation suggests potential benefit. The chronic active (refractory) gout population, while small, represents a true situation of medical need.

Primary Objective: To assess the safety of rilonacept in subjects with chronic, active gout, having at least one joint continuously inflamed.

Secondary Objectives: (1) To compare within subject changes in self-reported pain score (VAS) during the placebo run-in phase with the active treatment phase; (2) to assess the changes in the Subject and Physician Global Assessments during the placebo run-in and active treatment phases; (3) to assess the effect of rilonacept on C-reactive protein (CRP) and erythrocyte sedimentation rate (ESR) in subjects with chronic active gout.

Study Arms and Cohorts: Subjects are screened at Day −7; a two-week single blind placebo run-in begins at the Baseline visit (2×2 ml of placebo for rilonacept SQ); Single blind rilonacept 320 mg is administered subcutaneously at the Week 2 visit and then subjects self-inject 160 mg/week at home. Visits occur every two weeks through Week 8. PPD skin test, CXR, and inclusion/exclusion criteria are assessed at the Screening visit. Self-injection technique is taught at Screening and Baseline. Laboratory sample collections occur at Screening, Baseline, Weeks 2, 4, and 8. A follow-up visit occurs at Week 14.

Sample Size and Number of Sites: N=5 from up to 5 sites in the U.S.

Drug Supply: Placebo: 5 subjects×2 vials=10 vials+30% overage=13 vials; Rilonacept: 5 subjects×8 vials=48 vials+30% overage=66 vials, 3 vials per kit.

Subject Eligibility Criteria. Inclusion Criteria: (1) Male or female ≧21 years; (2) Chronis, active monoarticular or polyarticular gout (≧1 continuously inflamed joint due to gout, ±tophi); (3) VAS 10-point pain scale score of ≧3 (i.e., moderate or greater) due to joint pain/inflammation; (4) subjects for whom standard therapies are ineffective or associated with risks related to side effects.

Exclusion Criteria: (1) Organ transplant recipient; (2) current active infection; (3) serum creatinine <2.5 mg/dL; (4) other arthritic condition that could interfere with evaluations.

Primary Endpoint: Tolerability and safety profile of rilonacept.

Secondary Endpoints: (1) The change from Baseline to Week 8 in subject's pain score (10 cm VAS scale); (2) the change from Baseline to Week 8 in the Subject's Global Assessment; (3) the change from Baseline to Week 8 in the Physician's Global Assessment; (4) the change from Baseline to Week 8 in ESR and CRP.

Example 2

Safety of Rilonacept in Subjects with Chronic Active Gouty Arthritis

A 14 week, multi-center, non-randomized, single-blind, placebo-controlled, monosequence crossover study of rilonacept in subjects with chronic, active monoarticular or polyarticular gouty arthritis. Subjects receive 2 weeks of single-blind placebo followed by a loading dose of subcutaneous injections of 320 mg rilonacept, followed by weekly subcutaneous injections for 5 weeks of 160 mg rilonacept.Study Population. The study population included adult subjects (at least 18 years of age, male or female) with chronic, active monoarticular or polyarticular gouty arthritis diagnosed by a physician for at least 6 months with at least one continuously inflamed joint (self-reported or otherwise) for ≧4 weeks, a diagnosis of gout based on a history of the presence of crystals in the synovial fluid analysis, chronically elevated serum uric acid, and/or tophi; a visual analogue scale increment pain scale score of at least 3 due to joint pain/inflammation at both the Screening and Baseline Visits, and subjects for whom standard therapies for gout are less than effective or are associated with risks related to side effects.

Study Design. This study was a 14-week, multi-center, non-randomized, single-blind, placebo-controlled, monosequence crossover study of IL-1 trap (rilonacept) in subjects with chronic, active monoarticular or polyarticular gouty arthritis. Subjects received 2 weeks of single-blind placebo followed by a loading dose of subcutaneous injections of 320 mg rilonacept, followed by weekly subcutaneous injections for 5 weeks of 160 mg rilonacept. The study was conducted in approximately 12 sites in the U.S. This study includes a monosequence crossover design for the enrolled subjects: Treatment 1: Placebo injections for two weeks; Treatment 2: Injections of rilonacept for six weeks. Descriptive statistics was used to evaluate safety and efficacy of rilonacept in gout. Approximately 10 subjects were enrolled to receive placebo (2 weeks) and rilonacept (6 weeks) administered subcutaneously. Subjects received a total of two doses of placebo (on study days 0 and 7) and six doses of rilonacept on Days 14, 21, 28, 35, 42, and 49 during the study. Dose escalation was not allowed. Subjects were evaluated for efficacy and safety on a regular basis with clinical observations and laboratory measurements including anti-rilonacept antibodies, hs-CRP and ESR. The overall structure of the study included the following periods: Screening period: Screening procedures occurred within 7 days of start of study and included obtaining informed consent and evaluations to determine eligibility for study participation. Baseline: At the baseline visit (day 0), eligibility was confirmed, and the subject enrolled. Baseline assessments were made. The first injection of placebo was administered, and a vial of placebo dispensed. Placebo Treatment period: During the treatment period (Day 0 through Week 2), patients received placebo study medication, efficacy assessments were taken; safety and tolerability assessments were taken, including urine and blood samples for clinical laboratory testing. Active Treatment period: During the treatment period (Week 2 through Week 8), patients received active study medication, efficacy assessments were taken; safety and tolerability assessments were taken, including urine and blood samples for clinical laboratory testing. Blood samples were collected for biomarkers, IL-1 trap (rilonacept) plasma levels, and rilonacept antibodies. Follow-up: At Week 14, vital signs, bodyweight, adverse events, and concomitant medications assessments were taken. Blood samples were collected for biomarkers, rilonacept plasma levels, and rilonacept antibodies. The results are shown in Table 1. The first column lists the parameters assessed; column 2 (placebo response) compares the parameter measurements obtained at Week 2 with those measured at Day 0; column 3 (response of rilonacept) compares the parameter measurements obtained at Week 8 with those of Week 2; and column 4 (effect of withdrawal from treatment with rilonacept) compares the parameter measurements obtained at Week 14 with those obtained at Week 2.

Results. During treatment with placebo, there was no apparent trend toward improvement in any clinical parameter nor in CRP. Also, during treatment with placebo, there is no evidence of improvement. At the end of treatment with rilonacept, the proportion of responders is significantly better than a placebo response of 10%, regardless of how response was defined (p<0.01). Also, there was a significant reduction in patient's self-reported pain (p=0.02). When treatment with rilonacept was withdrawn, the trends toward efficacy waned and pain returned. These results suggest that placebo response is minimal, and reduction in pain is not observed until treatment with rilonacept is administered.

Example 3

Effectiveness of IL-1 Antagonist for Prevention of Gout Flares During Initiation of Allopurinol Therapy A multi-center, randomized, double-blind, placebo-controlled study in subjects with intercritical gout was conducted. 83 subjects were enrolled and treated with allopurinol orally once a day beginning on Day 1. Subjects were randomized in a 1:1 ratio to receive 160 mg rilonacept subcutaneously once a week or a placebo subcutaneously once a week for 16 weeks. Subjects received a loading dose on Day 1 (Baseline Visit) of rilonacept (320 mg given as two vials of 160 mg) or placebo (given in two equal volumes) (volumes 2 ml each) administered as subcutaneous injections.

Subjects in both treatment arms were started on a daily dose of 300 mg allopurinol on Day 1. The allopurinol dose was adjusted by 100 mg increments monthly to titrate subjects until they attained a serum uric acid level of less than 6 mg/dL. The maximum dose of allopurinol was 800 mg per day. For subjects with impaired renal function, the initial dose of allopurinol was adjusted based on the estimated creatinine clearance according to the Cockroft-Gault formula for estimating creatinine clearance.

Subjects would return to the clinic every 4 weeks for 16 weeks for study related procedures. Sites would call subjects every 2 weeks between visits for a brief review of their clinical status. A Safety Follow-up visit would occur 42 days after the last dose of study drug.

Subjects were instructed to call the study site upon first symptoms of a self-reported gout flare. A daily diary capturing pain, global well-being and symptoms of gout was completed by the subject starting on Day 1 of the flare until the resolution of all flare symptoms. Day 1 of the flare was defined as the onset of pain in any gouty joint and the end of the flare was defined as the day all pain in all joints resolved. All gout flares that occurred during the study from Baseline through the Terminal Visit (Visit 6) were followed to completion.

TABLE 1

| Assessment | Placebo Response | Rilonacept Response | | | Effects of Withdrawal from Treatment with Rilonacept |
|---|---|---|---|---|---|
| | Change Day 0-week 2 | Change Week 2-4 | Change week 2-4 | Change week 2-8 | Change week 8-14 |
| Subject's Assessment of Pain | 0.96 | 0.046 | 0.07 | 0.02 | 0.07 |
| Physician's Global Assessment | 0.09 | 0.4 | 0.8 | 0.2 | 0.02 |
| Subject's Global Assessment | 1.0 | 0.07 | 0.14 | 0.06 | 0.02 |
| Number of Affected Joints | 0.3 | 0.7 | 0.9 | 0.099 | 0.95 |
| Symptom-Adjusted Scores for Affected Joints (maximum of 3 per joint) | 0.2 | 0.7 | 0.8 | 0.04 | 0.3 |
| Severity-and-Symptom-Adjusted Scores for Affected Joints (maximum of 9 per joint) | 0.2 | 0.2 | 0.8 | 0.04 | 0.14 |
| Change from Baseline CRP | 0.5 | 0.002 | 0.004 | 0.004 | 0.04 |

Screening period. Screening procedures occurred within 2 weeks of start of study and included obtaining informed consent and evaluations to determine eligibility for study participation.

Baseline. At the baseline visit (day 1), eligibility was confirmed, and the subject randomized. Baseline assessments were made. The first administration (2 injections) of either 160 mg rilonacept (total loading dose of 320 mg rilonacept) or placebo was administered, and vials of the study medication dispensed. Subjects also received 300 mg allopurinol.

Treatment period. During the treatment period (Day 1 through Week 16), subjects received study medication (including daily allopurinol, adjusted as appropriate), efficacy assessments were taken; safety and tolerability assessments were taken, including urine and blood samples for clinical laboratory testing. Primary and secondary efficacy endpoints were measured at Week 12, but treatment continued through Week 16. All safety variables were summarized with time periods from Day 1 of study medicine to last dose date plus 42 days.

Follow-up. At Week 22, subject diaries were reviewed; vital signs, adverse events, and concomitant medications assessments were taken. Blood samples were collected for clinical laboratory assessments, rilonacept plasma levels and rilonacept antibodies assessments.

Primary efficacy variables. The primary efficacy variable was the mean number of gout flares from Day 1 to Week 12. The variable was calculated for each subject as number of flares observed from Day 1 to Week 12. For dropouts, only numbers of flares that occurred during the treatment period (defined as termination date-randomization date +1) were counted.

Secondary efficacy variables. (1). The proportion of subjects with one or more gout flares from Day 1 to Week 12. (2). The mean number of gout flares per month from Day 1 to Week 12. The variable was calculated for each subject as: Mean number of flares per month=(number of flares observed from Day 1 to Week 12)/(number of days subject was in study/28 days). (3). The mean number of gout flare days from Day 1 to Week 12. The variable for each subject was calculated as number of gout flares days from Day 1 to Week 12. Subjects with flares that started before the Week 12 visit and ended after the Week 12 visit included only days up to the Week 12 visit. (4). The mean number of gout flare days per month from Day 1 to Week 12. The mean number of gout flare days per month was calculated for each subject: Mean number of gout flares days per month from Day 1 to Week 12= (Number of flares days from Day 1 to Week 12)/(Number of days subject was in the study/28 days). Subjects with flares that started before the Week 12 visit and ended after the Week 12 visit included only days up to the Week 12 visit. (5). The mean number of days with the subject's pain score of 5 or more (from daily dairy) from Day 1 to Week 12. This was calculated for each subject as number of days with the subject's pain score 5 or more observed from Day 1 to Week 12. (6). The mean number of days per month with the subject's pain score of 5 or more (from daily dairy) from Day 1 to Week 12. This was calculated for each subject as: mean number of days per month with the subject's pain score 5 or more from Day 1 to Week 12=(Number of days with the subject's pain score of 5 or more observed)/(Number of days subject was in the study/28 days).

Exploratory Efficacy Variables. Exploratory variables included time to first gout flare, percentage of subjects with usage, and duration of NSAIDS and glucocorticoids during study, proportion of subjects with uric acid levels less than 6 mg/dL by visit, and percentage of total gout flares by number of visits. The time period for all these variables was from Day 1 to Week 12.

Results are shown in Tables 2 and 3. Rilonacept achieved a dramatic 81% reduction in gout flares, from 0.79 to 0.15 (Table 2; p=0.0006). [1]P-value is based on the two-sample t-test; [2]Gout-Free-Flare: no gout flare during time interval; [3]P-value based on Fisher's exact test.

TABLE 2

| Time Interval Day 1 to Week 12 | Rilonacept | Placebo | P-value |
| --- | --- | --- | --- |
| Mean Number of Gout Flares | 0.15 ± 0.358 (n = 41) | 0.79 ± 1.071 (n = 42) | 0.0006[1] |

TABLE 3

| Time Interval Day 1 to Week 12 | Rilonacept | Placebo | P-value[3] |
| --- | --- | --- | --- |
| Subjects Gout-Flare-Free[2] | 85.4% (n = 35) | 54.8% (n = 23) | 0.0037 |
| Subjects with ≧ Gout Flare | 14.6% (n = 6) | 45.2% (n = 19) | |

What is claimed is:

1. A method of treating drug-induced gout flares, comprising administering to a subject being treated with a therapeutic agent for gout, a therapeutically effective amount of an interleukin 1 (IL-1) antagonist, wherein the incidence of the gout flare is reduced by at least about 50% relative to not administering the IL-1 antagonist.

2. The method of claim 1, wherein administration of the IL-1 antagonist is subcutaneous or intravenous administration.

3. The method of claim 2, wherein administration is single or multiple subcutaneous injections or intravenous infusions 4. The method of claim 1, wherein said therapeutically effective amount of an IL-1 antagonist is between 1 to 30 mg/kg.

5. The method of claim 4, wherein a administration is a one or more subcutaneous or intravenous dose(s) of a therapeutically effective amount of IL-1 antagonist of up to about 100 to 2000 mg.

6. The method of claim 5, wherein an initial dose is between about 80-500 mg of the IL-1 antagonist administered subcutaneously, and one or more subsequent doses of 40-250 mg are administered subcutaneously.

7. The method of claim 1, wherein the IL-1 antagonist is rilonacept.

8. The method of claim 1, wherein the incidence of the drug-induced gout flare is reduced by at least about 60% relative to not administering the IL-1 antagonist.

9. The method of claim 8, wherein the incidence of the drug-induced gout flare is reduced by at least about 75% relative to not administering the IL-1 antagonist.

10. The method of claim 9, wherein the incidence of the drug-induced gout flare is reduced by at least about 80% relative to not administering the IL-1 antagonist.

11. The method of claim 6, wherein frequency of administration of said subsequent doses is weekly, biweekly or monthly.

12. The method of claim 1, wherein said therapeutic agent for gout is a xanthine oxidase inhibitor.

13. The method of claim 12, wherein said xanthine oxidase inhibitor is allopurinol or febuxostat.

14. The method of claim 1, wherein said therapeutic agent for gout is a urate oxidase.

15. The method of claim 14, wherein said urate oxidase is uricase, rasburicase or pegylated uricase.

16. The method of claim 1, wherein said therapeutic agent for gout is a uricosuric agent.

17. The method of claim 16, wherein said uricosuric agent is probenecid, sulfinpyrazone, benzbromarone or fenofibrate.

* * * * *

SEQUENCE LISTING

```
<160> NUMBER OF SEQ ID NOS: 26

<210> SEQ ID NO 1
<211> LENGTH: 2733
<212> TYPE: DNA
<213> ORGANISM: Homo sapiens

<400> SEQUENCE: 1 atg gtg ctt ctg tgg tgt gta gtg agt ctc tac ttt tat gga atc ctg      48 caa agt gat gcc tca gaa cgc tgc gat gac tgg gga cta gac acc atg      96 agg caa atc caa gtg ttt gaa gat gag cca gct cgc atc aag tgc cca     144 ctc ttt gaa cac ttc ttg aaa ttc aac tac agc aca gcc cat tca gct     192
```

-continued

| | |
|---|---|
| ggc ctt act ctg atc tgg tat tgg act agg cag gac cgg gac ctt gag | 240 |
| gag cca att aac ttc cgc ctc ccc gag aac cgc att agt aag gag aaa | 288 |
| gat gtg ctg tgg ttc cgg ccc act ctc ctc aat gac act ggc aac tat | 336 |
| acc tgc atg tta agg aac act aca tat tgc agc aaa gtt gca ttt ccc | 384 |
| ttg gaa gtt gtt caa aaa gac agc tgt ttc aat tcc ccc atg aaa ctc | 432 |
| cca gtg cat aaa ctg tat ata gaa tat ggc att cag agg atc act tgt | 480 |
| cca aat gta gat gga tat ttt cct tcc agt gtc aaa ccg act atc act | 528 |
| tgg tat atg ggc tgt tat aaa ata cag aat ttt aat aat gta ata ccc | 576 |
| gaa ggt atg aac ttg agt ttc ctc att gcc tta att tca aat aat gga | 624 |
| aat tac aca tgt gtt gtt aca tat cca gaa aat gga cgt acg ttt cat | 672 |
| ctc acc agg act ctg act gta aag gta gta ggc tct cca aaa aat gca | 720 |
| gtg ccc cct gtg atc cat tca cct aat gat cat gtg gtc tat gag aaa | 768 |
| gaa cca gga gag gag cta ctc att ccc tgt acg gtc tat ttt agt ttt | 816 |
| ctg atg gat tct cgc aat gag gtt tgg tgg acc att gat gga aaa aaa | 864 |
| cct gat gac atc act att gat gtc acc att aac gaa agt ata agt cat | 912 |
| agt aga aca gaa gat gaa aca aga act cag att ttg agc atc aag aaa | 960 |
| gtt acc tct gag gat ctc aag cgc agc tat gtc tgt cat gct aga agt | 1008 |
| gcc aaa ggc gaa gtt gcc aaa gca gcc aag gtg aag cag aaa gtg cca | 1056 |
| gct cca aga tac aca gtg tcc ggt ggc gcg cct atg ctg agc gag gct | 1104 |
| gat aaa tgc aag gaa cgt gaa gaa aaa ata att tta gtg tca tct gca | 1152 |
| aat gaa att gat gtt cgt ccc tgt cct ctt aac cca aat gaa cac aaa | 1200 |
| ggc act ata act tgg tat aag gat gac agc aag aca cct gta tct aca | 1248 |
| gaa caa gcc tcc agg att cat caa cac aaa gag aaa ctt tgg ttt gtt | 1296 |
| cct gct aag gtg gag gat tca gga cat tac tat tgc gtg gta aga aat | 1344 |
| tca tct tac tgc ctc aga att aaa ata agt gca aaa ttt gtg gag aat | 1392 |
| gag cct aac tta tgt tat aat gca caa gcc ata ttt aag cag aaa cta | 1440 |
| ccc gtt gca gga gac gga gga ctt gtg tgc cct tat atg gag ttt ttt | 1488 |
| aaa aat gaa aat aat gag tta cct aaa tta cag tgg tat aag gat tgc | 1536 |
| aaa cct cta ctt ctt gac aat ata cac ttt agt gga gtc aaa gat agg | 1584 |
| ctc atc gtg atg aat gtg gct gaa aag cat aga ggg aac tat act tgt | 1632 |
| cat gca tcc tac aca tac ttg ggc aag caa tat cct att acc cgg gta | 1680 |
| ata gaa ttt att act cta gag gaa aac aaa ccc aca agg cct gtg att | 1728 |
| gtg agc cca gct aat gag aca atg gaa gta gac ttg gga tcc cag ata | 1776 |
| caa ttg atc tgt aat gtc acc ggc cag ttg agt gac att gct tac tgg | 1824 |
| aag tgg aat ggg tca gta att gat gaa gat gac cca gtg cta ggg gaa | 1872 |
| gac tat tac agt gtg gaa aat cct gca aac aaa aga agg agt acc ctc | 1920 |
| atc aca gtg ctt aat ata tcg gaa att gag agt aga ttt tat aaa cat | 1968 |
| cca ttt acc tgt ttt gcc aag aat aca cat ggt ata gat gca gca tat | 2016 |
| atc cag tta ata tat cca gtc act aat tcc gga gac aaa act cac aca | 2064 |
| tgc cca ccg tgc cca gca cct gaa ctc ctg ggg gga ccg tca gtc ttc | 2112 |

```
ctc ttc ccc cca aaa ccc aag gac acc ctc atg atc tcc cgg acc cct    2160
gag gtc aca tgc gtg gtg gtg gac gtg agc cac gaa gac cct gag gtc    2208
aag ttc aac tgg tac gtg gac ggc gtg gag gtg cat aat gcc aag aca    2256
aag ccg cgg gag gag cag tac aac agc acg tac cgt gtg gtc agc gtc    2304
ctc acc gtc ctg cac cag gac tgg ctg aat ggc aag gag tac aag tgc    2352
aag gtc tcc aac aaa gcc ctc cca gcc ccc atc gag aaa acc atc tcc    2400
aaa gcc aaa ggg cag ccc cga gaa cca cag gtg tac acc ctg ccc cca    2448
tcc cgg gag gag atg acc aag aac cag gtc agc ctg acc tgc ctg gtc    2496
aaa ggc ttc tat ccc agc gac atc gcc gtg gag tgg gag agc aat ggg    2544
cag ccg gag aac aac tac aag acc acg cct ccc gtg ctg gac tcc gac    2592
ggc tcc ttc ttc ctc tat agc aag ctc acc gtg gac aag agc agg tgg    2640
cag cag ggg aac gtc ttc tca tgc tcc gtg atg cat gag gct ctg cac    2688
aac cac tac acg cag aag agc ctc tcc ctg tct ccg ggt aaa           2730
tga                                                                2733
```

<210> SEQ ID NO 2
<211> LENGTH: 910
<212> TYPE: PRT
<213> ORGANISM: Homo sapiens

<400> SEQUENCE: 2

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
        20                  25                  30

Arg Gln Ile Gln Val Phe Glu Asp Glu Pro Ala Arg Ile Lys Cys Pro
    35                  40                  45

Leu Phe Glu His Phe Leu Lys Phe Asn Tyr Ser Thr Ala His Ser Ala
50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220
```

```
Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
245                 250                 255                 260

Glu Pro Gly Glu Glu Leu Leu Ile Pro Cys Thr Val Tyr Phe Ser Phe
                265                 270

Leu Met Asp Ser Arg Asn Glu Val Trp Trp Thr Ile Asp Gly Lys Lys
275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
325                 330                 335

Ala Lys Gly Glu Val Ala Lys Ala Ala Lys Val Lys Gln Lys Val Pro
340                 345                 350

Ala Pro Arg Tyr Thr Val Ser Gly Gly Ala Pro Met Leu Ser Glu Ala
355                 360                 365

Asp Lys Cys Lys Glu Arg Glu Glu Lys Ile Ile Leu Val Ser Ser Ala
370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
405                 410                 415

Glu Gln Ala Ser Arg Ile His Gln His Lys Glu Lys Leu Trp Phe Val
420                 425                 430

Pro Ala Lys Val Glu Asp Ser Gly His Tyr Tyr Cys Val Val Arg Asn
435                 440                 445

Ser Ser Tyr Cys Leu Arg Ile Lys Ile Ser Ala Lys Phe Val Glu Asn
450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
485                 490                 495

Lys Asn Glu Asn Asn Glu Leu Pro Lys Leu Gln Trp Tyr Lys Asp Cys
500                 505                 510

Lys Pro Leu Leu Leu Asp Asn Ile His Phe Ser Gly Val Lys Asp Arg
515                 520                 525

Leu Ile Val Met Asn Val Ala Glu Lys His Arg Gly Asn Tyr Thr Cys
530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
565                 570                 575

Val Ser Pro Ala Asn Glu Thr Met Glu Val Asp Leu Gly Ser Gln Ile
580                 585                 590

Gln Leu Ile Cys Asn Val Thr Gly Gln Leu Ser Asp Ile Ala Tyr Trp
595                 600                 605

Lys Trp Asn Gly Ser Val Ile Asp Glu Asp Pro Val Leu Gly Glu
610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
```

```
                    645                 650                 655
Pro Phe Thr Cys Phe Ala Lys Asn Thr His Gly Ile Asp Ala Ala Tyr
660                 665                 670

Ile Gln Leu Ile Tyr Pro Val Thr Asn Ser Gly Asp Lys Thr His Thr
675                 680                 685

Cys Pro Pro Cys Pro Ala Pro Glu Leu Leu Gly Gly Pro Ser Val Phe
690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
725                 730                 735

Lys Phe Asn Trp Tyr Val Asp Gly Val Glu Val His Asn Ala Lys Thr
740                 745                 750

Lys Pro Arg Glu Glu Gln Tyr Asn Ser Thr Tyr Arg Val Val Ser Val
755                 760                 765

Leu Thr Val Leu His Gln Asp Trp Leu Asn Gly Lys Glu Tyr Lys Cys
770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
805                 810                 815

Ser Arg Glu Glu Met Thr Lys Asn Gln Val Ser Leu Thr Cys Leu Val
820                 825                 830

Lys Gly Phe Tyr Pro Ser Asp Ile Ala Val Glu Trp Glu Ser Asn Gly
835                 840                 845

Gln Pro Glu Asn Asn Tyr Lys Thr Thr Pro Pro Val Leu Asp Ser Asp
850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
885                 890                 895

Asn His Tyr Thr Gln Lys Ser Leu Ser Leu Ser Pro Gly Lys
900                 905                 910

<210> SEQ ID NO 3
<211> LENGTH: 2703
<212> TYPE: DNA
<213> ORGANISM: Homo sapiens

<400> SEQUENCE: 3
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta aacttggta aggatgac       180 agcaagacac ctgtatctac agaacaagcc tccaggattc atcaacacaa agagaaactt    240
tggtttgttc ctgctaaggt ggaggattca ggacattact attgcgtggt aagaaattca    300
tcttactgcc tcagaattaa aataagtgca aaatttgtgg agaatgagcc taacttatgt    360
tataatgcac aagccatatt taagcagaaa ctacccgttg caggagacgg aggacttgtg    420
tgcccttata tggagttttt taaaaatgaa aataatgagt acctaaaatt acagtggtat    480
aaggattgca aacctctact tcttgacaat atacacttta gtggagtcaa agataggctc    540
atcgtgatga atggctga aaagcataga gggaactata cttgtcatgc atcctacaca    600
tacttgggca agcaatatcc tattacccgg gtaatagaat ttattactct agaggaaaac    660
```

```
aaacccacaa ggcctgtgat tgtgagccca gctaatgaga caatggaagt agacttggga      720
tcccagatac aattgatctg taatgtcacc ggccagttga gtgacattgc ttactggaag      780
tggaatgggt cagtaattga tgaagatgac ccagtgctag gggaagacta ttacagtgtg      840
gaaaatcctg caaacaaaag aaggagtacc ctcatcacag tgcttaatat atcggaaatt      900
gagagtagat tttataaaca tccatttacc tgttttgcca agaatacaca tggtatagat      960
gcagcatata tccagttaat atatccagtc actaattcag aacgctgcga tgactgggga     1020
ctagacacca tgaggcaaat ccaagtgttt gaagatgagc cagctcgcat caagtgccca     1080
ctctttgaac acttcttgaa attcaactac agcacagccc attcagctgg ccttactctg     1140
atctggtatt ggactaggca ggaccgggac cttgaggagc caattaactt ccgcctcccc     1200
gagaaccgca ttagtaagga aaagatgtg ctgtggttcc ggcccactct cctcaatgac     1260
actggcaact atacctgcat gttaaggaac actacatatt gcagcaaagt tgcatttccc     1320
ttggaagttg ttcaaaaaga cagctgtttc aattccccca tgaaactccc agtgcataaa     1380
ctgtatatag aatatggcat tcagaggatc acttgtccaa atgtagatgg atattttcct     1440
tccagtgtca aaccgactat cacttggtat atgggctgtt ataaaataca gaattttaat     1500
aatgtaatac ccgaaggtat gaacttgagt ttcctcattg ccttaatttc aaataatgga     1560
aattacacat gtgttgttac atatccagaa aatggacgta cgtttcatct caccaggact     1620
ctgactgtaa aggtagtagg ctctccaaaa aatgcagtgc cccctgtgat ccattcacct     1680
aatgatcatg tggtctatga aaagaaccca ggagaggagc tactcattcc ctgtacggtc     1740
tattttagtt ttctgatgga ttctcgcaat gaggtttggt ggaccattga tggaaaaaaa     1800
cctgatgaca tcactattga tgtcaccatt aacgaaagta taagtcatag tagaacagaa     1860
gatgaaacaa gaactcagat tttgagcatc aagaaagtta cctctgagga tctcaagcgc     1920
agctatgtct gtcatgctag aagtgccaaa ggcgaagttg ccaaagcagc caaggtgaag     1980
cagaaagtgc cagctccaag atacacagtg gaatccggag acaaaactca cacatgccca     2040
ccgtgcccag cacctgaact cctgggggga ccgtcagtct tcctcttccc cccaaaaccc     2100
aaggacaccc tcatgatctc ccggacccct gaggtcacat gcgtggtggt ggacgtgagc     2160
cacgaagacc ctgaggtcaa gttcaactgg tacgtggacg gcgtggaggt gcataatgcc     2220
aagacaaagc cgcgggagga gcagtacaac agcacgtacc gtgtggtcag cgtcctcacc     2280
gtcctgcacc aggactggct gaatggcaag gagtacaagt gcaaggtctc caacaaagcc     2340
ctcccagccc ccatcgagaa aaccatctcc aaagccaaag ggcagccccg agaaccacag     2400
gtgtacaccc tgcccccatc ccgggaggag atgaccaaga accaggtcag cctgacctgc     2460
ctggtcaaag gcttctatcc cagcgacatc gccgtggagt gggagagcaa tgggcagccg     2520
gagaacaact acaagaccac gcctcccgtg ctggactccg acggctcctt cttcctctat     2580
agcaagctca ccgtggacaa gagcaggtgg cagcagggga acgtcttctc atgctccgtg     2640
atgcatgagg ctctgcacaa ccactacacg cagaagagcc tctccctgtc tccgggtaaa     2700
tga                                                                   2703
```

<210> SEQ ID NO 4
<211> LENGTH: 900
<212> TYPE: PRT
<213> ORGANISM: Homo sapiens

<400> SEQUENCE: 4

-continued

```
Met Val Leu Leu Arg Leu Ile Cys Phe Ile Ala Leu Ile Ser Ser
1               5                   10                  15

Leu Glu Ala Asp Lys Cys Lys Glu Arg Glu Glu Lys Ile Ile Leu Val
20                  25                  30

Ser Ser Ala Asn Glu Ile Asp Val Arg Pro Cys Pro Leu Asn Pro Asn
35                  40                  45

Glu His Lys Gly Thr Ile Thr Trp Tyr Lys Asp Asp Ser Lys Thr Pro
50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
85                  90                  95

Val Arg Asn Ser Ser Tyr Cys Leu Arg Ile Lys Ile Ser Ala Lys Phe
100                 105                 110

Val Glu Asn Glu Pro Asn Leu Cys Tyr Asn Ala Gln Ala Ile Phe Lys
115                 120                 125

Gln Lys Leu Pro Val Ala Gly Asp Gly Gly Leu Val Cys Pro Tyr Met
130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
165                 170                 175

Lys Asp Arg Leu Ile Val Met Asn Val Ala Glu Lys His Arg Gly Asn
180                 185                 190

Tyr Thr Cys His Ala Ser Tyr Thr Tyr Leu Gly Lys Gln Tyr Pro Ile
195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
245                 250                 255

Ala Tyr Trp Lys Trp Asn Gly Ser Val Ile Asp Glu Asp Pro Val
260                 265                 270

Leu Gly Glu Asp Tyr Tyr Ser Val Glu Asn Pro Ala Asn Lys Arg Arg
275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
325                 330                 335

Asp Asp Trp Gly Leu Asp Thr Met Arg Gln Ile Gln Val Phe Glu Asp
340                 345                 350

Glu Pro Ala Arg Ile Lys Cys Pro Leu Phe Glu His Phe Leu Lys Phe
355                 360                 365

Asn Tyr Ser Thr Ala His Ser Ala Gly Leu Thr Leu Ile Trp Tyr Trp
370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
405                 410                 415

Leu Leu Asn Asp Thr Gly Asn Tyr Thr Cys Met Leu Arg Asn Thr Thr
```

```
                420               425               430
Tyr Cys Ser Lys Val Ala Phe Pro Leu Glu Val Gln Lys Asp Ser
435               440               445

Cys Phe Asn Ser Pro Met Lys Leu Pro Val His Lys Leu Tyr Ile Glu
450               455               460

Tyr Gly Ile Gln Arg Ile Thr Cys Pro Asn Val Asp Gly Tyr Phe Pro
465               470               475               480

Ser Ser Val Lys Pro Thr Ile Thr Trp Tyr Met Gly Cys Tyr Lys Ile
485               490               495

Gln Asn Phe Asn Asn Val Ile Pro Glu Gly Met Asn Leu Ser Phe Leu
500               505               510

Ile Ala Leu Ile Ser Asn Asn Gly Asn Tyr Thr Cys Val Val Thr Tyr
515               520               525

Pro Glu Asn Gly Arg Thr Phe His Leu Thr Arg Thr Leu Thr Val Lys
530               535               540

Val Val Gly Ser Pro Lys Asn Ala Val Pro Pro Val Ile His Ser Pro
545               550               555               560

Asn Asp His Val Val Tyr Glu Lys Glu Pro Gly Glu Glu Leu Leu Ile
565               570               575

Pro Cys Thr Val Tyr Phe Ser Phe Leu Met Asp Ser Arg Asn Glu Val
580               585               590

Trp Trp Thr Ile Asp Gly Lys Lys Pro Asp Asp Ile Thr Ile Asp Val
595               600               605

Thr Ile Asn Glu Ser Ile Ser His Ser Arg Thr Glu Asp Glu Thr Arg
610               615               620

Thr Gln Ile Leu Ser Ile Lys Lys Val Thr Ser Glu Asp Leu Lys Arg
625               630               635               640

Ser Tyr Val Cys His Ala Arg Ser Ala Lys Gly Glu Val Ala Lys Ala
645               650               655

Ala Lys Val Lys Gln Lys Val Pro Ala Pro Arg Tyr Thr Val Glu Ser
660               665               670

Gly Asp Lys Thr His Thr Cys Pro Pro Cys Pro Ala Pro Glu Leu Leu
675               680               685

Gly Gly Pro Ser Val Phe Leu Phe Pro Pro Lys Pro Lys Asp Thr Leu
690               695               700

Met Ile Ser Arg Thr Pro Glu Val Thr Cys Val Val Val Asp Val Ser
705               710               715               720

His Glu Asp Pro Glu Val Lys Phe Asn Trp Tyr Val Asp Gly Val Glu
725               730               735

Val His Asn Ala Lys Thr Lys Pro Arg Glu Glu Gln Tyr Asn Ser Thr
740               745               750

Tyr Arg Val Val Ser Val Leu Thr Val Leu His Gln Asp Trp Leu Asn
755               760               765

Gly Lys Glu Tyr Lys Cys Lys Val Ser Asn Lys Ala Leu Pro Ala Pro
770               775               780

Ile Glu Lys Thr Ile Ser Lys Ala Lys Gly Gln Pro Arg Glu Pro Gln
785               790               795               800

Val Tyr Thr Leu Pro Pro Ser Arg Glu Glu Met Thr Lys Asn Gln Val
805               810               815

Ser Leu Thr Cys Leu Val Lys Gly Phe Tyr Pro Ser Asp Ile Ala Val
820               825               830

Glu Trp Glu Ser Asn Gly Gln Pro Glu Asn Asn Tyr Lys Thr Thr Pro
835               840               845
```

```
Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
885                 890                 895

Ser Pro Gly Lys
900

<210> SEQ ID NO 5
<211> LENGTH: 2709
<212> TYPE: DNA
<213> ORGANISM: Homo sapiens

<400> SEQUENCE: 5
```

| | | | | | |
|---|---|---|---|---|---|
| atggtgttac | tcagacttat | ttgtttcata | gctctactga | tttcttctct | ggaggctgat | 60 |
| aaatgcaagg | aacgtgaaga | aaaaataatt | ttagtgtcat | ctgcaaatga | aattgatgtt | 120 |
| cgtccctgtc | ctcttaaccc | aaatgaacac | aaaggcacta | aacttggta | taaggatgac | 180 |
| agcaagacac | ctgtatctac | agaacaagcc | tccaggattc | atcaacacaa | agagaaactt | 240 |
| tggtttgttc | ctgctaaggt | ggaggattca | ggacattact | attgcgtggt | aagaaattca | 300 |
| tcttactgcc | tcagaattaa | aataagtgca | aaatttgtgg | agaatgagcc | taacttatgt | 360 |
| tataatgcac | aagccatatt | taagcagaaa | ctacccgttg | caggagacgg | aggacttgtg | 420 |
| tgcccttata | tggagttttt | taaaaatgaa | ataatgagt | acctaaaatt | acagtggtat | 480 |
| aaggattgca | aacctctact | tcttgacaat | atacactta | gtggagtcaa | agataggctc | 540 |
| atcgtgatga | atgtggctga | aaagcataga | gggaactata | cttgtcatgc | atcctacaca | 600 |
| tacttgggca | agcaatatcc | tattacccgg | gtaatagaat | ttattactct | agaggaaaac | 660 |
| aaacccacaa | ggcctgtgat | tgtgagccca | gctaatgaga | caatggaagt | agacttggga | 720 |
| tcccagatac | aattgatctg | taatgtcacc | ggccagttga | gtgacattgc | ttactggaag | 780 |
| tggaatgggt | cagtaattga | tgaagatgac | ccagtgctag | ggaagactaa | tacagtgtg | 840 |
| gaaaatcctg | caaacaaaag | aaggagtacc | ctcatcacag | tgcttaatat | atcggaaatt | 900 |
| gagagtagat | tttataaaca | tccatttacc | tgttttgcca | agaatacaca | tggtatagat | 960 |
| gcagcatata | tccagttaat | atatccagtc | actaattcag | aacgctgcga | tgactgggga | 1020 |
| ctagacacca | tgaggcaaat | ccaagtgttt | gaagatgagc | cagctcgcat | caagtgccca | 1080 |
| ctctttgaac | acttcttgaa | attcaactac | agcacagccc | attcagctgg | ccttactctg | 1140 |
| atctggtatt | ggactaggca | ggaccgggac | cttgaggagc | caattaactt | ccgcctcccc | 1200 |
| gagaaccgca | ttagtaagga | aagatgtg | ctgtggttcc | ggcccactct | cctcaatgac | 1260 |
| actggcaact | atacctgcat | gttaaggaac | actacatatt | gcagcaaagt | tgcatttccc | 1320 |
| ttggaagttg | ttcaaaaaga | cagctgtttc | aattcccca | tgaaactccc | agtgcataaa | 1380 |
| ctgtatatag | aatatggcat | tcagaggatc | acttgtccaa | atgtagatgg | atattttcct | 1440 |
| tccagtgtca | aaccgactat | cacttggtat | atgggctgtt | ataaaatca | gaattttaat | 1500 |
| aatgtaatac | ccgaaggtat | gaacttgagt | ttcctcattg | ccttaatttc | aaataatgga | 1560 |
| aattacacat | gtgttgttac | atatccagaa | aatggacgta | cgtttcatct | caccaggact | 1620 |
| ctgactgtaa | aggtagtagg | ctctccaaaa | aatgcagtgc | ccctgtgat | ccattcacct | 1680 |
| aatgatcatg | tggtctatga | aaagaaccca | ggagaggagc | tactcattcc | ctgtacggtc | 1740 |

```
tattttagtt ttctgatgga ttctcgcaat gaggtttggt ggaccattga tggaaaaaaa    1800
cctgatgaca tcactattga tgtcaccatt aacgaaagta taagtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaaa    1980
cagaaagtgc cagctccaag atacacagtg gaatccggag agtccaaata cggtccgcca    2040
tgcccatcat gcccagcacc tgagttcctg ggggaccat cagtcttcct gttccccca     2100 aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga caactacaa gaccacgcct cccgtgctgg actccgacgg ctccttcttc     2580
ctctacagca ggctaaccgt ggacaagagc aggtggcagg aggggaatgt cttctcatgc    2640
tccgtgatgc atgaggctct gcacaaccac tacacacaga gagcctctc cctgtctctg     2700 ggtaaatga                                                           2709

<210> SEQ ID NO 6
<211> LENGTH: 902
<212> TYPE: PRT
<213> ORGANISM: Homo sapiens

<400> SEQUENCE: 6

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
```

-continued

```
            195                 200                 205
Thr Arg Val Ile Glu Phe Ile Thr Leu Glu Glu Asn Lys Pro Thr Arg
210                 215                 220
Pro Val Ile Val Ser Pro Ala Asn Glu Thr Met Glu Val Asp Leu Gly
225                 230                 235                 240
Ser Gln Ile Gln Leu Ile Cys Asn Val Thr Gly Gln Leu Ser Asp Ile
245                 250                 255
Ala Tyr Trp Lys Trp Asn Gly Ser Val Ile Asp Glu Asp Pro Val
260                 265                 270
Leu Gly Glu Asp Tyr Tyr Ser Val Glu Asn Pro Ala Asn Lys Arg Arg
275                 280                 285
Ser Thr Leu Ile Thr Val Leu Asn Ile Ser Glu Ile Glu Ser Arg Phe
290                 295                 300
Tyr Lys His Pro Phe Thr Cys Phe Ala Lys Asn Thr His Gly Ile Asp
305                 310                 315                 320
Ala Ala Tyr Ile Gln Leu Ile Tyr Pro Val Thr Asn Ser Glu Arg Cys
325                 330                 335
Asp Asp Trp Gly Leu Asp Thr Met Arg Gln Ile Gln Val Phe Glu Asp
340                 345                 350
Glu Pro Ala Arg Ile Lys Cys Pro Leu Phe Glu His Phe Leu Lys Phe
355                 360                 365
Asn Tyr Ser Thr Ala His Ser Ala Gly Leu Thr Leu Ile Trp Tyr Trp
370                 375                 380
Thr Arg Gln Asp Arg Asp Leu Glu Glu Pro Ile Asn Phe Arg Leu Pro
385                 390                 395                 400
Glu Asn Arg Ile Ser Lys Glu Lys Asp Val Leu Trp Phe Arg Pro Thr
405                 410                 415
Leu Leu Asn Asp Thr Gly Asn Tyr Thr Cys Met Leu Arg Asn Thr Thr
420                 425                 430
Tyr Cys Ser Lys Val Ala Phe Pro Leu Glu Val Gln Lys Asp Ser
435                 440                 445
Cys Phe Asn Ser Pro Met Lys Leu Pro Val His Lys Leu Tyr Ile Glu
450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
485                 490                 495
Gln Asn Phe Asn Asn Val Ile Pro Glu Gly Met Asn Leu Ser Phe Leu
500                 505                 510
Ile Ala Leu Ile Ser Asn Asn Gly Asn Tyr Thr Cys Val Val Thr Tyr
515                 520                 525
Pro Glu Asn Gly Arg Thr Phe His Leu Thr Arg Thr Leu Thr Val Lys
530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
565                 570                 575
Pro Cys Thr Val Tyr Phe Ser Phe Leu Met Asp Ser Arg Asn Glu Val
580                 585                 590
Trp Trp Thr Ile Asp Gly Lys Lys Pro Asp Asp Ile Thr Ile Asp Val
595                 600                 605
Thr Ile Asn Glu Ser Ile Ser His Ser Arg Thr Glu Asp Glu Thr Arg
610                 615                 620
```

```
Thr Gln Ile Leu Ser Ile Lys Lys Val Thr Glu Asp Leu Lys Arg
625                 630                 635                 640

Ser Tyr Val Cys His Ala Arg Ser Ala Lys Gly Glu Val Ala Lys Ala
645                 650                 655

Ala Lys Val Lys Gln Lys Val Pro Ala Pro Arg Tyr Thr Val Glu Ser
660                 665                 670

Gly Glu Ser Lys Tyr Gly Pro Pro Cys Pro Ser Cys Pro Ala Pro Glu
675                 680                 685

Phe Leu Gly Gly Pro Ser Val Phe Leu Phe Pro Pro Lys Pro Lys Asp
690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
725                 730                 735

Val Glu Val His Asn Ala Lys Thr Lys Pro Arg Glu Glu Gln Phe Asn
740                 745                 750

Ser Thr Tyr Arg Val Val Ser Val Leu Thr Val Leu His Gln Asp Trp
755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
805                 810                 815

Gln Val Ser Leu Thr Cys Leu Val Lys Gly Phe Tyr Pro Ser Asp Ile
820                 825                 830

Ala Val Glu Trp Glu Ser Asn Gly Gln Pro Glu Asn Asn Tyr Lys Thr
835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
885                 890                 895

Ser Leu Ser Leu Gly Lys
900

<210> SEQ ID NO 7
<211> LENGTH: 2709
<212> TYPE: DNA
<213> ORGANISM: Homo sapiens

<400> SEQUENCE: 7
atggtgttac tcagacttat ttgtttcata gctctactga tttcttctct ggaggctgat    60
aaatgcaagg aacgtgaaga aaaataatt ttagtgtcat ctgcaaatga aattgatgtt   120
cgtccctgtc ctcttaaccc aaatgaacac aaaggcacta aacttggta taaggatgac   180 agcaagacac ctgtatctac agaacaagcc tccaggattc atcaacacaa agagaaactt   240
tggtttgttc ctgctaaggt ggaggattca ggacattact attgcgtggt aagaattca   300 tcttactgcc tcagaattaa aataagtgca aaatttgtgg agaatgagcc taacttatgt   360
tataatgcac aagccatatt taagcagaaa ctacccgttg caggagacgg aggcttgtg   420 tgccccttata tggagttttt taaaaatgaa ataatgagt tacctaaatt acagtggtat   480
```

| | |
|---|---|
| aaggattgca aacctctact tcttgacaat atacacttta gtggagtcaa agataggctc | 540 |
| atcgtgatga atgtggctga aaagcataga gggaactata cttgtcatgc atcctacaca | 600 |
| tacttgggca agcaatatcc tattacccgg gtaatagaat ttattactct agaggaaaac | 660 |
| aaacccacaa ggcctgtgat tgtgagccca gctaatgaga caatggaagt agacttggga | 720 |
| tcccagatac aattgatctg taatgtcacc ggccagttga gtgacattgc ttactggaag | 780 |
| tggaatgggt cagtaattga tgaagatgac ccagtgctag gggaagacta ttacagtgtg | 840 |
| gaaaatcctg caaacaaaag aaggagtacc ctcatcacag tgcttaatat atcggaaatt | 900 |
| gagagtagat tttataaaca tccatttacc tgttttgcca agaatacaca tggtatagat | 960 |
| gcagcatata tccagttaat atatccagtc actaattcag aacgctgcga tgactgggga | 1020 |
| ctagacacca tgaggcaaat ccaagtgttt gaagatgagc cagctcgcat caagtgccca | 1080 |
| ctctttgaac acttcttgaa attcaactac agcacagccc attcagctgg ccttactctg | 1140 |
| atctggtatt ggactaggca ggaccgggac cttgaggagc caattaactt ccgcctcccc | 1200 |
| gagaaccgca ttagtaagga aaagatgtg ctgtggttcc ggcccactct cctcaatgac | 1260 |
| actggcaact atacctgcat gttaaggaac actacatatt gcagcaaagt tgcatttccc | 1320 |
| ttggaagttg ttcaaaaaga cagctgtttc aattccccca tgaaactccc agtgcataaa | 1380 |
| ctgtatatag aatatggcat tcagaggatc acttgtccaa atgtagatgg atattttcct | 1440 |
| tccagtgtca aaccgactat cacttggtat atgggctgtt ataaaataca gaattttaat | 1500 |
| aatgtaatac ccgaaggtat gaacttgagt ttcctcattg ccttaattc aaataatgga | 1560 |
| aattacacat gtgttgttac atatccagaa aatggacgta cgtttcatct caccaggact | 1620 |
| ctgactgtaa aggtagtagg ctctccaaaa aatgcagtgc ccctgtgat ccattcacct | 1680 |
| aatgatcatg tggtctatga gaaagaacca ggagaggagc tactcattcc ctgtacggtc | 1740 |
| tattttagtt ttctgatgga ttctcgcaat gaggtttggt ggaccattga tggaaaaaaa | 1800 |
| cctgatgaca tcactattga tgtcaccatt aacgaaagta taagtcatag tagaacagaa | 1860 |
| gatgaaacaa gaactcagat tttgagcatc aagaaagtta cctctgagga tctcaagcgc | 1920 |
| agctatgtct gtcatgctag aagtgccaaa ggcgaagttg ccaaagcagc caaggtgaag | 1980 |
| cagaaagtgc cagctccaag atacacagtg gaatccggag agtccaaata cggtccgcca | 2040 |
| tgcccaccat gcccagcacc tgagttcctg ggggaccat cagtcttcct gttcccccca | 2100 |
| aaacccaagg acactctcat gatctcccgg acccctgagg tcacgtgcgt ggtggtggac | 2160 |
| gtgagccagg aagaccccga ggtccagttc aactggtacg tggatggcgt ggaggtgcat | 2220 |
| aatgccaaga caaagccgcg ggaggagcag ttcaacagca cgtaccgtgt ggtcagcgtc | 2280 |
| ctcaccgtcc tgcaccagga ctggctgaac ggcaaggagt acaagtgcaa ggtctccaac | 2340 |
| aaaggcctcc cgtcctccat cgagaaaacc atctccaaag ccaaagggca gccccgagag | 2400 |
| ccacaggtgt acaccctgcc cccatcccag gaggagatga ccaagaacca ggtcagcctg | 2460 |
| acctgcctgg tcaaaggctt ctaccccagc gacatcgccg tggagtggga gagcaatggg | 2520 |
| cagccggaga acaactacaa gaccacgcct cccgtgctgg actccgacgg ctccttcttc | 2580 |
| ctctacagca ggctaaccgt ggacaagagc aggtggcagg aggggaatgt cttctcatgc | 2640 |
| tccgtgatgc atgaggctct gcacaaccac tacacacaga gagcctctc cctgtctctg | 2700 |
| ggtaaatga | 2709 |

<210> SEQ ID NO 8
<211> LENGTH: 902

<212> TYPE: PRT
<213> ORGANISM: Homo sapiens

<400> SEQUENCE: 8

```
Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
        20                  25                  30

Ser Ser Ala Asn Glu Ile Asp Val Arg Pro Cys Pro Leu Asn Pro Asn
    35                  40                  45

Glu His Lys Gly Thr Ile Thr Trp Tyr Lys Asp Asp Ser Lys Thr Pro
50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
            85                  90                  95

Val Arg Asn Ser Ser Tyr Cys Leu Arg Ile Lys Ile Ser Ala Lys Phe
        100                 105                 110

Val Glu Asn Glu Pro Asn Leu Cys Tyr Asn Ala Gln Ala Ile Phe Lys
    115                 120                 125

Gln Lys Leu Pro Val Ala Gly Asp Gly Gly Leu Val Cys Pro Tyr Met
130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
            165                 170                 175

Lys Asp Arg Leu Ile Val Met Asn Val Ala Glu Lys His Arg Gly Asn
        180                 185                 190

Tyr Thr Cys His Ala Ser Tyr Thr Tyr Leu Gly Lys Gln Tyr Pro Ile
    195                 200                 205

Thr Arg Val Ile Glu Phe Ile Thr Leu Glu Glu Asn Lys Pro Thr Arg
210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
            245                 250                 255

Ala Tyr Trp Lys Trp Asn Gly Ser Val Ile Asp Glu Asp Asp Pro Val
        260                 265                 270

Leu Gly Glu Asp Tyr Tyr Ser Val Glu Asn Pro Ala Asn Lys Arg Arg
    275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
            325                 330                 335

Asp Asp Trp Gly Leu Asp Thr Met Arg Gln Ile Gln Val Phe Glu Asp
        340                 345                 350

Glu Pro Ala Arg Ile Lys Cys Pro Leu Phe Glu His Phe Leu Lys Phe
    355                 360                 365

Asn Tyr Ser Thr Ala His Ser Ala Gly Leu Thr Leu Ile Trp Tyr Trp
370                 375                 380

Thr Arg Gln Asp Arg Asp Leu Glu Glu Pro Ile Asn Phe Arg Leu Pro
385                 390                 395                 400
```

-continued

```
Glu Asn Arg Ile Ser Lys Glu Lys Asp Val Leu Trp Phe Arg Pro Thr
405                 410                 415
Leu Leu Asn Asp Thr Gly Asn Tyr Thr Cys Met Leu Arg Asn Thr Thr
420                 425                 430
Tyr Cys Ser Lys Val Ala Phe Pro Leu Glu Val Val Gln Lys Asp Ser
435                 440                 445
Cys Phe Asn Ser Pro Met Lys Leu Pro Val His Lys Leu Tyr Ile Glu
450                 455                 460
Tyr Gly Ile Gln Arg Ile Thr Cys Pro Asn Val Asp Gly Tyr Phe Pro
465                 470                 475                 480
Ser Ser Val Lys Pro Thr Ile Thr Trp Tyr Met Gly Cys Tyr Lys Ile
485                 490                 495
Gln Asn Phe Asn Asn Val Ile Pro Glu Gly Met Asn Leu Ser Phe Leu
500                 505                 510
Ile Ala Leu Ile Ser Asn Asn Gly Asn Tyr Thr Cys Val Val Thr Tyr
515                 520                 525
Pro Glu Asn Gly Arg Thr Phe His Leu Thr Arg Thr Leu Thr Val Lys
530                 535                 540
Val Val Gly Ser Pro Lys Asn Ala Val Pro Pro Val Ile His Ser Pro
545                 550                 555                 560
Asn Asp His Val Val Tyr Glu Lys Glu Pro Gly Glu Glu Leu Leu Ile
565                 570                 575
Pro Cys Thr Val Tyr Phe Ser Phe Leu Met Asp Ser Arg Asn Glu Val
580                 585                 590
Trp Trp Thr Ile Asp Gly Lys Lys Pro Asp Asp Ile Thr Ile Asp Val
595                 600                 605
Thr Ile Asn Glu Ser Ile Ser His Ser Arg Thr Glu Asp Glu Thr Arg
610                 615                 620
Thr Gln Ile Leu Ser Ile Lys Lys Val Thr Ser Glu Asp Leu Lys Arg
625                 630                 635                 640
Ser Tyr Val Cys His Ala Arg Ser Ala Lys Gly Glu Val Ala Lys Ala
645                 650                 655
Ala Lys Val Lys Gln Lys Val Pro Ala Pro Arg Tyr Thr Val Glu Ser
660                 665                 670
Gly Glu Ser Lys Tyr Gly Pro Pro Cys Pro Pro Cys Pro Ala Pro Glu
675                 680                 685
Phe Leu Gly Gly Pro Ser Val Phe Leu Phe Pro Pro Lys Pro Lys Asp
690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
725                 730                 735
Val Glu Val His Asn Ala Lys Thr Lys Pro Arg Glu Glu Gln Phe Asn
740                 745                 750
Ser Thr Tyr Arg Val Val Ser Val Leu Thr Val Leu His Gln Asp Trp
755                 760                 765
Leu Asn Gly Lys Glu Tyr Lys Cys Lys Val Ser Asn Lys Gly Leu Pro
770                 775                 780
Ser Ser Ile Glu Lys Thr Ile Ser Lys Ala Lys Gly Gln Pro Arg Glu
785                 790                 795                 800
Pro Gln Val Tyr Thr Leu Pro Pro Ser Gln Glu Glu Met Thr Lys Asn
805                 810                 815
```

```
Gln Val Ser Leu Thr Cys Leu Val Lys Gly Phe Tyr Pro Ser Asp Ile
820                 825                 830
Ala Val Glu Trp Glu Ser Asn Gly Gln Pro Glu Asn Asn Tyr Lys Thr
835                 840                 845
Thr Pro Pro Val Leu Asp Ser Asp Gly Ser Phe Phe Leu Tyr Ser Arg
850                 855                 860
Leu Thr Val Asp Lys Ser Arg Trp Gln Glu Gly Asn Val Phe Ser Cys
865                 870                 875                 880
Ser Val Met His Glu Ala Leu His Asn His Tyr Thr Gln Lys Ser Leu
885                 890                 895
Ser Leu Ser Leu Gly Lys
900

<210> SEQ ID NO 9
<211> LENGTH: 2703
<212> TYPE: DNA
<213> ORGANISM: Homo sapiens

<400> SEQUENCE: 9
```

| | | | | | |
|---|---|---|---|---|---|
| atggtgcttc | tgtggtgtgt | agtgagtctc | tacttttatg | gaatcctgca | aagtgatgcc     60 |
| tcagaacgct | gcgatgactg | gggactagac | accatgaggc | aaatccaagt | gtttgaagat    120 |
| gagccagctc | gcatcaagtg | cccactcttt | gaacacttct | tgaaattcaa | ctacagcaca    180 |
| gcccattcag | ctggccttac | tctgatctgg | tattggacta | ggcaggaccg | ggaccttgag    240 |
| gagccaatta | acttccgcct | ccccgagaac | cgcattagta | aggagaaaga | tgtgctgtgg    300 |
| ttccggccca | ctctcctcaa | tgacactggc | aactatacct | gcatgttaag | gaacactaca    360 |
| tattgcagca | aagttgcatt | tcccttggaa | gttgttcaaa | aagacagctg | tttcaattcc    420 |
| cccatgaaac | tcccagtgca | taaactgtat | atagaatatg | gcattcagag | gatcacttgt    480 |
| ccaaatgtag | atgatatttt | tccttccagt | gtcaaaccga | ctatcacttg | gtatatgggc    540 |
| tgttataaaa | tacagaattt | taataatgta | atacccgaag | gtatgaactt | gagtttcctc    600 |
| attgccttaa | tttcaaataa | tggaaattac | acatgtgttg | ttacatatcc | agaaaatgga    660 |
| cgtacgtttc | atctcaccag | gactctgact | gtaaaggtag | taggctctcc | aaaaaatgca    720 |
| gtgccccctg | tgatccattc | acctaatgat | catgtggtct | atgagaaaga | accaggagag    780 |
| gagctactca | ttccctgtac | ggtctatttt | agttttctga | tggattctcg | caatgaggtt    840 |
| tggtggacca | ttgatggaaa | aaacctgat | gacatcacta | ttgatgtcac | cattaacgaa    900 |
| agtataagtc | atagtagaac | agaagatgaa | acaagaactc | agattttgag | catcaagaaa    960 |
| gttacctctg | aggatctcaa | gcgcagctat | gtctgtcatg | ctagaagtgc | caaaggcgaa   1020 |
| gttgccaaag | cagccaaggt | gaagcagaaa | gtgccagctc | aagatacac | agtggaaaaa   1080 |
| tgcaaggaac | gtgaagaaaa | aataattta | gtgagctcag | caaatgaaat | cgatgttcgt   1140 |
| ccctgtcctc | ttaacccaaa | tgaacacaaa | ggcactataa | cttggtataa | ggatgacagc   1200 |
| aagacacctg | tatctacaga | acaagcctcc | aggattcatc | aacacaaaga | gaaactttgg   1260 |
| tttgttcctg | ctaaggtgga | ggattcagga | cattactatt | gcgtggtaag | aaattcatct   1320 |
| tactgcctca | gaattaaaat | aagtgcaaaa | tttgtggaga | atgagcctaa | cttatgttat   1380 |
| aatgcacaag | ccatatttaa | gcagaaacta | cccgttgcag | agacggagg | acttgtgtgc   1440 |
| ccttatatgg | agttttttaa | aaatgaaaat | aatgagttac | ctaaattaca | gtggtataag   1500 |
| gattgcaaac | tctacttct | tgacaatata | cactttagtg | gagtcaaaga | taggctcatc   1560 |
| gtgatgaatg | tggctgaaaa | gcatagaggg | aactatactt | gtcatgcatc | ctacacatac   1620 |

```
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
aatcctgcaa acaaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag acaaaactca cacatgccca    2040
ccgtgcccag cacctgaact cctgggggga ccgtcagtct tcctcttccc cccaaaaccc    2100
aaggacaccc tcatgatctc ccggacccct gaggtcacat gcgtggtggt ggacgtgagc    2160
cacgaagacc ctgaggtcaa gttcaactgg tacgtggacg gcgtggaggt gcataatgcc    2220
aagacaaagc cgcgggagga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag gcagccccg agaaccacag    2400 gtgtacaccc tgcccccatc ccgggatgag ctgaccaaga accaggtcag cctgacctgc    2460
ctggtcaaag gcttctatcc cagcgacatc gccgtggagt gggagagcaa tgggcagccg    2520
gagaacaact acaagaccac gcctcccgtg ctggactccg acggctcctt cttcctctac    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                 2703

<210> SEQ ID NO 10
<211> LENGTH: 900
<212> TYPE: PRT
<213> ORGANISM: Homo sapiens

<400> SEQUENCE: 10

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175
```

```
Trp Tyr Met Gly Cys Tyr Lys Ile Gln Asn Phe Asn Val Ile Pro
180                 185                 190

Glu Gly Met Asn Leu Ser Phe Leu Ile Ala Leu Ile Ser Asn Asn Gly
195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
245                 250                 255

Glu Pro Gly Glu Glu Leu Leu Ile Pro Cys Thr Val Tyr Phe Ser Phe
260                 265                 270

Leu Met Asp Ser Arg Asn Glu Val Trp Trp Thr Ile Asp Gly Lys Lys
275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
325                 330                 335

Ala Lys Gly Glu Val Ala Lys Ala Ala Lys Val Lys Gln Lys Val Pro
340                 345                 350

Ala Pro Arg Tyr Thr Val Glu Lys Cys Lys Glu Arg Glu Glu Lys Ile
355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
405                 410                 415

Glu Lys Leu Trp Phe Val Pro Ala Lys Val Glu Asp Ser Gly His Tyr
420                 425                 430

Tyr Cys Val Val Arg Asn Ser Ser Tyr Cys Leu Arg Ile Lys Ile Ser
435                 440                 445

Ala Lys Phe Val Glu Asn Glu Pro Asn Leu Cys Tyr Asn Ala Gln Ala
450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
485                 490                 495

Gln Trp Tyr Lys Asp Cys Lys Pro Leu Leu Leu Asp Asn Ile His Phe
500                 505                 510

Ser Gly Val Lys Asp Arg Leu Ile Val Met Asn Val Ala Glu Lys His
515                 520                 525

Arg Gly Asn Tyr Thr Cys His Ala Ser Tyr Thr Tyr Leu Gly Lys Gln
530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
565                 570                 575

Asp Leu Gly Ser Gln Ile Gln Leu Ile Cys Asn Val Thr Gly Gln Leu
580                 585                 590
```

```
Ser Asp Ile Ala Tyr Trp Lys Trp Asn Gly Ser Val Ile Asp Glu Asp
595                 600                 605

Asp Pro Val Leu Gly Glu Asp Tyr Tyr Ser Val Glu Asn Pro Ala Asn
610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
645                 650                 655

Gly Ile Asp Ala Ala Tyr Ile Gln Leu Ile Tyr Pro Val Thr Asn Ser
660                 665                 670

Gly Asp Lys Thr His Thr Cys Pro Pro Cys Pro Ala Pro Glu Leu Leu
675                 680                 685

Gly Gly Pro Ser Val Phe Leu Phe Pro Pro Lys Pro Lys Asp Thr Leu
690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
725                 730                 735

Val His Asn Ala Lys Thr Lys Pro Arg Glu Glu Gln Tyr Asn Ser Thr
740                 745                 750

Tyr Arg Val Val Ser Val Leu Thr Val Leu His Gln Asp Trp Leu Asn
755                 760                 765

Gly Lys Glu Tyr Lys Cys Lys Val Ser Asn Lys Ala Leu Pro Ala Pro
770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
805                 810                 815

Ser Leu Thr Cys Leu Val Lys Gly Phe Tyr Pro Ser Asp Ile Ala Val
820                 825                 830

Glu Trp Glu Ser Asn Gly Gln Pro Glu Asn Asn Tyr Lys Thr Thr Pro
835                 840                 845

Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
885                 890                 895

Ser Pro Gly Lys
900

<210> SEQ ID NO 11
<211> LENGTH: 2709
<212> TYPE: DNA
<213> ORGANISM: Homo sapiens

<400> SEQUENCE: 11
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactatacct gcatgttaag gaacactaca     360
```

```
tattgcagca aagttgcatt tcccttggaa gttgttcaaa agacagctg tttcaattcc      420 cccatgaaac tcccagtgca taaactgtat atagaatatg gcattcagag gatcacttgt      480
ccaaatgtag atggatattt tccttccagt gtcaaaccga ctatcacttg gtatatgggc      540
tgttataaaa tacagaattt taataatgta atacccgaag gtatgaactt gagtttcctc      600
attgccttaa tttcaaataa tggaaattac acatgtgttg ttacatatcc agaaaatgga      660
cgtacgtttc atctcaccag gactctgact gtaaaggtag taggctctcc aaaaaatgca      720 gtgcccctg tgatccattc acctaatgat catgtggtct atgagaaaga accaggagag       780
gagctactca ttccctgtac ggtctatttt agttttctga tggattctcg caatgaggtt      840
tggtggacca ttgatggaaa aaacctgat gacatcacta ttgatgtcac cattaacgaa       900
agtataagtc atagtagaac agaagatgaa acaagaactc agattttgag catcaagaaa      960
gttacctctg aggatctcaa gcgcagctat gtctgtcatg ctagaagtgc caaaggcgaa     1020
gttgccaaag cagccaaggt gaagcagaaa gtgccagctc aagatacac agtggaaaaa      1080 tgcaaggaac gtgaagaaaa aataatttta gtgagctcag caaatgaaat cgatgttcgt     1140
ccctgtcctc ttaacccaaa tgaacacaaa ggcactataa cttggtataa ggatgacagc     1200
aagacacctg tatctacaga caagcctcc aggattcatc aacacaaaga gaaactttgg      1260
tttgttcctg ctaaggtgga ggattcagga cattactatt gcgtggtaag aaattcatct     1320
tactgcctca gaattaaaat aagtgcaaaa tttgtggaga atgagcctaa cttatgttat     1380
aatgcacaag ccatatttaa gcagaaacta cccgttgcag gagacggagg acttgtgtgc     1440
ccttatatgg agtttttaa aaatgaaaat aatgagttac ctaaattaca gtggtataag     1500
gattgcaaac ctctacttct tgacaatata cactttagtg gagtcaaaga taggctcatc     1560
gtgatgaatg tggctgaaaa gcatagaggg aactatactt gtcatgcatc ctacacatac     1620
ttgggcaagc aatatcctat tacccgggta atagaatttta ttactctaga ggaaaacaaa     1680
cccacaaggc ctgtgattgt gagcccagct aatgagacaa tggaagtaga cttgggatcc     1740
cagatacaat tgatctgtaa tgtcaccggc cagttgagtg acattgctta ctggaagtgg     1800
aatgggtcag taattgatga agatgaccca gtgctagggg aagactatta cagtgtggaa     1860
aatcctgcaa acaaaagaag gagtaccctc atcacagtgc ttaatatatc ggaaattgag     1920
agtagatttt ataaacatcc atttacctgt tttgccaaga atacacatgg tatagatgca     1980
gcatatatcc agttaatata tccagtcact aattccggag agtccaaata cggtccgcca     2040
tgcccatcat gcccagcacc tgagttcctg gggggaccat cagtcttcct gttcccccca     2100
aaacccaagg acactctcat gatctcccgg acccctgagg tcacgtgcgt ggtggtggac     2160
gtgagccagg aagacccga ggtccagttc aactggtacg tggatggcgt ggaggtgcat      2220
aatgccaaga caaagccgcg ggaggagcag ttcaacagca cgtaccgtgt ggtcagcgtc     2280
ctcaccgtcc tgcaccagga ctggctgaac ggcaaggagt acaagtgcaa ggtctccaac     2340
aaaggcctcc cgtcctccat cgagaaaacc atctccaaag ccaaagggca gccccgagag     2400
ccacaggtgt acaccctgcc cccatcccag gaggagatga ccaagaacca ggtcagcctg     2460
acctgcctgg tcaaaggctt ctaccccagc gacatcgccg tggagtggga gagcaatggg     2520
cagccggaga acaactacaa gaccacgcct cccgtgctgg actccgacgg ctccttcttc     2580
ctctacagca ggctaaccgt ggacaagagc aggtggcagg aggggaatgt cttctcatgc     2640
tccgtgatgc atgaggctct gcacaaccac tacacacaga gagcctctc cctgtctctg      2700
```

```
ggtaaatga                                                        2709
```

<210> SEQ ID NO 12
<211> LENGTH: 902
<212> TYPE: PRT
<213> ORGANISM: Homo sapiens

<400> SEQUENCE: 12

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

-continued

```
Ile Leu Val Ser Ser Ala Asn Glu Ile Asp Val Arg Pro Cys Pro Leu
370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
405                 410                 415
Glu Lys Leu Trp Phe Val Pro Ala Lys Val Glu Asp Ser Gly His Tyr
420                 425                 430
Tyr Cys Val Val Arg Asn Ser Ser Tyr Cys Leu Arg Ile Lys Ile Ser
435                 440                 445
Ala Lys Phe Val Glu Asn Glu Pro Asn Leu Cys Tyr Asn Ala Gln Ala
450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Asn Glu Leu Pro Lys Leu
485                 490                 495
Gln Trp Tyr Lys Asp Cys Lys Pro Leu Leu Leu Asp Asn Ile His Phe
500                 505                 510
Ser Gly Val Lys Asp Arg Leu Ile Val Met Asn Val Ala Glu Lys His
515                 520                 525
Arg Gly Asn Tyr Thr Cys His Ala Ser Tyr Thr Tyr Leu Gly Lys Gln
530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
565                 570                 575
Asp Leu Gly Ser Gln Ile Gln Leu Ile Cys Asn Val Thr Gly Gln Leu
580                 585                 590
Ser Asp Ile Ala Tyr Trp Lys Trp Asn Gly Ser Val Ile Asp Glu Asp
595                 600                 605
Asp Pro Val Leu Gly Glu Asp Tyr Tyr Ser Val Glu Asn Pro Ala Asn
610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
645                 650                 655
Gly Ile Asp Ala Ala Tyr Ile Gln Leu Ile Tyr Pro Val Thr Asn Ser
660                 665                 670
Gly Glu Ser Lys Tyr Gly Pro Pro Cys Pro Ser Cys Pro Ala Pro Glu
675                 680                 685
Phe Leu Gly Gly Pro Ser Val Phe Leu Phe Pro Pro Lys Pro Lys Asp
690                 695                 700
Thr Leu Met Ile Ser Arg Thr Pro Glu Val Thr Cys Val Val Val Asp
705                 710                 715                 720
Val Ser Gln Glu Asp Pro Glu Val Gln Phe Asn Trp Tyr Val Asp Gly
725                 730                 735
Val Glu Val His Asn Ala Lys Thr Lys Pro Arg Glu Glu Gln Phe Asn
740                 745                 750
Ser Thr Tyr Arg Val Val Ser Val Leu Thr Val Leu His Gln Asp Trp
755                 760                 765
Leu Asn Gly Lys Glu Tyr Lys Cys Lys Val Ser Asn Lys Gly Leu Pro
770                 775                 780
Ser Ser Ile Glu Lys Thr Ile Ser Lys Ala Lys Gly Gln Pro Arg Glu
```

```
                785                 790                 795                 800
Pro Gln Val Tyr Thr Leu Pro Pro Ser Gln Glu Glu Met Thr Lys Asn
805                 810                 815

Gln Val Ser Leu Thr Cys Leu Val Lys Gly Phe Tyr Pro Ser Asp Ile
820                 825                 830

Ala Val Glu Trp Glu Ser Asn Gly Gln Pro Glu Asn Asn Tyr Lys Thr
835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
885                 890                 895

Ser Leu Ser Leu Gly Lys
900

<210> SEQ ID NO 13
<211> LENGTH: 2709
<212> TYPE: DNA
<213> ORGANISM: Homo sapiens

<400> SEQUENCE: 13
atggtgcttc tgtggtgtgt agtgagtctc tactttatg gaatcctgca aagtgatgcc        60
tcagaacgct gcgatgactg gggactagac accatgaggc aaatccaagt gtttgaagat       120
gagccagctc gcatcaagtg cccactcttt gaacacttct tgaaattcaa ctacagcaca       180
gcccattcag ctggccttac tctgatctgg tattggacta ggcaggaccg ggaccttgag       240
gagccaatta acttccgcct ccccgagaac cgcattagta ggagaaaga gtgctgtgtgg       300 ttccggccca ctctcctcaa tgacactggc aactatacct gcatgttaag gaacactaca       360
tattgcagca aagttgcatt tcccttggaa gttgttcaaa aagacagctg tttcaattcc       420
cccatgaaac tcccagtgca taaactgtat atagaatatg gcattcagag gatcacttgt       480
ccaaatgtag atgatatttt ccttccagt gtcaaaccga ctatcacttg gtatatgggc       540
tgttataaaa tacagaattt taataatgta atacccgaag gtatgaactt gagtttcctc       600
attgccttaa tttcaaataa tggaaattac acatgtgttg ttacatatcc agaaaatgga       660
cgtacgtttc atctcaccag gactctgact gtaaaggtag taggctctcc aaaaaatgca       720 gtgcccctg tgatccattc acctaatgat catgtggtct atgagaaaga accaggagag       780
gagctactca ttccctgtac ggtctatttt agttttctga tggattctcg caatgaggtt       840
tggtggacca ttgatggaaa aaacctgat gacatcacta ttgatgtcac cattaacgaa       900
agtataagtc atagtagaac agaagatgaa acaagaactc agattttgag catcaagaaa       960
gttacctctg aggatctcaa gcgcagctat gtctgtcatg ctagaagtgc caaaggcgaa      1020
gttgccaaag cagccaaggt gaagcagaaa gtgccagctc aagatacac agtggaaaaa      1080 tgcaaggaac gtgaagaaaa aataatttta gtgagctcag caaatgaaat cgatgttcgt      1140
ccctgtcctc ttaacccaaa tgaacacaaa ggcactataa cttggtataa ggatgacagc      1200
aagacacctg tatctacaga acaagcctcc aggattcatc aacacaaaga gaaactttgg      1260
tttgttcctg ctaaggtgga ggattcagga cattactatt gcgtggtaag aaattcatct      1320
tactgcctca gaattaaaat aagtgcaaaa tttgtggaga atgagcctaa cttatgttat      1380
aatgcacaag ccatatttaa gcagaaaacta cccgttgcag agacggagg acttgtgtgc      1440
```

-continued

```
ccttatatgg agtttttta aaatgaaaat aatgagttac ctaaattaca gtggtataag    1500
gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
aatgggtcag taattgatga agatgaccca gtgctagggg aagactatta cagtgtggaa    1860
aatcctgcaa acaaaagaag gagtaccctc atcacagtgc ttaatatatc ggaaattgag    1920
agtagatttt ataaacatcc atttacctgt tttgccaaga atacacatgg tatagatgca    1980
gcatatatcc agttaatata tccagtcact aattccggag agtccaaata cggtccgcca    2040
tgcccaccat gcccagcacc tgagttcctg gggggaccat cagtcttcct gttccccca    2100 aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca ggctaaccgt ggacaagagc aggtggcagg aggggaatgt cttctcatgc    2640
tccgtgatgc atgaggctct gcacaaccac tacacacaga agagcctctc cctgtctctg    2700
ggtaaatga                                                           2709
```

<210> SEQ ID NO 14
<211> LENGTH: 902
<212> TYPE: PRT
<213> ORGANISM: Homo sapiens

<400> SEQUENCE: 14

```
Met Val Leu Leu Trp Cys Val Val Ser Leu Tyr Phe Tyr Gly Ile Leu
1               5                   10                  15

Gln Ser Asp Ala Ser Glu Arg Cys Asp Trp Gly Leu Asp Thr Met
        20                  25                  30

Arg Gln Ile Gln Val Phe Glu Asp Glu Pro Ala Arg Ile Lys Cys Pro
    35                  40                  45

Leu Phe Glu His Phe Leu Lys Phe Asn Tyr Ser Thr Ala His Ser Ala
50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140
```

```
Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
165                 170                 175

Trp Tyr Met Gly Cys Tyr Lys Ile Gln Asn Phe Asn Asn Val Ile Pro
180                 185                 190

Glu Gly Met Asn Leu Ser Phe Leu Ile Ala Leu Ile Ser Asn Asn Gly
195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
245                 250                 255

Glu Pro Gly Glu Glu Leu Leu Ile Pro Cys Thr Val Tyr Phe Ser Phe
260                 265                 270

Leu Met Asp Ser Arg Asn Glu Val Trp Trp Thr Ile Asp Gly Lys Lys
275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
325                 330                 335

Ala Lys Gly Glu Val Ala Lys Ala Ala Lys Val Lys Gln Lys Val Pro
340                 345                 350

Ala Pro Arg Tyr Thr Val Glu Lys Cys Lys Glu Arg Glu Glu Lys Ile
355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
405                 410                 415

Glu Lys Leu Trp Phe Val Pro Ala Lys Val Glu Asp Ser Gly His Tyr
420                 425                 430

Tyr Cys Val Val Arg Asn Ser Ser Tyr Cys Leu Arg Ile Lys Ile Ser
435                 440                 445

Ala Lys Phe Val Glu Asn Glu Pro Asn Leu Cys Tyr Asn Ala Gln Ala
450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
485                 490                 495

Gln Trp Tyr Lys Asp Cys Lys Pro Leu Leu Leu Asp Asn Ile His Phe
500                 505                 510

Ser Gly Val Lys Asp Arg Leu Ile Val Met Asn Val Ala Glu Lys His
515                 520                 525

Arg Gly Asn Tyr Thr Cys His Ala Ser Tyr Thr Tyr Leu Gly Lys Gln
530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
```

```
                565                 570                 575
Asp Leu Gly Ser Gln Ile Gln Leu Ile Cys Asn Val Thr Gly Gln Leu
580                 585                 590

Ser Asp Ile Ala Tyr Trp Lys Trp Asn Gly Ser Val Ile Asp Glu Asp
595                 600                 605

Asp Pro Val Leu Gly Glu Asp Tyr Tyr Ser Val Glu Asn Pro Ala Asn
610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
645                 650                 655

Gly Ile Asp Ala Ala Tyr Ile Gln Leu Ile Tyr Pro Val Thr Asn Ser
660                 665                 670

Gly Glu Ser Lys Tyr Gly Pro Pro Cys Pro Pro Cys Pro Ala Pro Glu
675                 680                 685

Phe Leu Gly Gly Pro Ser Val Phe Leu Phe Pro Pro Lys Pro Lys Asp
690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
725                 730                 735

Val Glu Val His Asn Ala Lys Thr Lys Pro Arg Glu Glu Gln Phe Asn
740                 745                 750

Ser Thr Tyr Arg Val Val Ser Val Leu Thr Val Leu His Gln Asp Trp
755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
805                 810                 815

Gln Val Ser Leu Thr Cys Leu Val Lys Gly Phe Tyr Pro Ser Asp Ile
820                 825                 830

Ala Val Glu Trp Glu Ser Asn Gly Gln Pro Glu Asn Asn Tyr Lys Thr
835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
885                 890                 895

Ser Leu Ser Leu Gly Lys
900

<210> SEQ ID NO 15
<211> LENGTH: 2748
<212> TYPE: DNA
<213> ORGANISM: Homo sapiens

<400> SEQUENCE: 15
atggtgcgct tgtacgtgtt ggtaatggga gtttctgcct tcaccttca gcctgcggca      60 cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
```

```
gtcagccccc gcatcaacct gacatggcat aaaaatgact ctgctaggac ggtcccagga   240
gaagaagaga cacggatgtg ggcccaggac ggtgctctgt ggcttctgcc agccttgcag   300
gaggactctg gcacctacgt ctgcactact agaaatgctt cttactgtga caaaatgtcc   360
attgagctca gagtttttga gaatacagat gctttcctgc cgttcatctc atacccgcaa   420
attttaacct tgtcaacctc tggggtatta gtatgccctg acctgagtga attcacccgt   480
gacaaaactg acgtgaagat tcaatggtac aaggattctc ttcttttgga taaagacaat   540
gagaaatttc taagtgtgag ggggaccact cacttactcg tacacgatgt ggccctggaa   600
gatgctggct attaccgctg tgtcctgaca tttgcccatg aaggccagca atacaacatc   660
actaggagta ttgagctacg catcaagaaa aaaaagaag agaccattcc tgtgatcatt   720
tcccccctca agaccatatc agcttctctg gggtcaagac tgacaatccc atgtaaggtg   780
tttctgggaa ccggcacacc cttaaccacc atgctgtggt ggacggccaa tgacacccac   840
atagagagcg cctacccggg aggccgcgtg accgaggggc cacgccagga atattcagaa   900
aataatgaga actacattga agtgccattg attttgatc ctgtcacaag agaggatttg   960
cacatggatt ttaaatgtgt tgtccataat accctgagtt tcagacact acgcaccaca   1020 gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagacaaa actcacacat gcccaccgtg cccagcacct   2100
gaactcctgg ggggaccgtc agtcttcctc ttccccccaa acccaaggga cccctcatg   2160 atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca agccctccc agccccatc   2400 gagaaaacca tctccaaagc caagggcag ccccgagaac acaggtgta cacctgccc   2460 ccatcccggg atgagctgac caagaaccag gtcagcctga cctgcctggt caaaggcttc   2520
tatcccagcg acatcgccgt ggagtgggag agcaatgggc agccggagaa caactacaag   2580
```

```
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
cacaaccact acacgcagaa gagcctctcc ctgtctccgg gtaaatga                2748
```

<210> SEQ ID NO 16
<211> LENGTH: 915
<212> TYPE: PRT
<213> ORGANISM: Homo sapiens

<400> SEQUENCE: 16

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
```

```
        340             345                 350
Asp Asp Trp Gly Leu Asp Thr Met Arg Gln Ile Gln Val Phe Glu Asp
355                 360                 365

Glu Pro Ala Arg Ile Lys Cys Pro Leu Phe Glu His Phe Leu Lys Phe
370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
405                 410                 415

Glu Asn Arg Ile Ser Lys Glu Lys Asp Val Leu Trp Phe Arg Pro Thr
420                 425                 430

Leu Leu Asn Asp Thr Gly Asn Tyr Thr Cys Met Leu Arg Asn Thr Thr
435                 440                 445

Tyr Cys Ser Lys Val Ala Phe Pro Leu Glu Val Val Gln Lys Asp Ser
450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
485                 490                 495

Ser Ser Val Lys Pro Thr Ile Thr Trp Tyr Met Gly Cys Tyr Lys Ile
500                 505                 510

Gln Asn Phe Asn Asn Val Ile Pro Glu Gly Met Asn Leu Ser Phe Leu
515                 520                 525

Ile Ala Leu Ile Ser Asn Asn Gly Asn Tyr Thr Cys Val Val Thr Tyr
530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
565                 570                 575

Asn Asp His Val Val Tyr Glu Lys Glu Pro Gly Glu Glu Leu Leu Ile
580                 585                 590

Pro Cys Thr Val Tyr Phe Ser Phe Leu Met Asp Ser Arg Asn Glu Val
595                 600                 605

Trp Trp Thr Ile Asp Gly Lys Lys Pro Asp Asp Ile Thr Ile Asp Val
610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
645                 650                 655

Ser Tyr Val Cys His Ala Arg Ser Ala Lys Gly Glu Val Ala Lys Ala
660                 665                 670

Ala Lys Val Lys Gln Lys Val Pro Ala Pro Arg Tyr Thr Val Ser Gly
675                 680                 685

Asp Lys Thr His Thr Cys Pro Pro Cys Pro Ala Pro Glu Leu Leu Gly
690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
725                 730                 735

Glu Asp Pro Glu Val Lys Phe Asn Trp Tyr Val Asp Gly Val Glu Val
740                 745                 750

His Asn Ala Lys Thr Lys Pro Arg Glu Glu Gln Tyr Asn Ser Thr Tyr
755                 760                 765
```

```
Arg Val Val Ser Val Leu Thr Val Leu His Gln Asp Trp Leu Asn Gly
770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
805                 810                 815
Tyr Thr Leu Pro Pro Ser Arg Asp Glu Leu Thr Lys Asn Gln Val Ser
820                 825                 830
Leu Thr Cys Leu Val Lys Gly Phe Tyr Pro Ser Asp Ile Ala Val Glu
835                 840                 845
Trp Glu Ser Asn Gly Gln Pro Glu Asn Asn Tyr Lys Thr Thr Pro Pro
850                 855                 860
Val Leu Asp Ser Asp Gly Ser Phe Phe Leu Tyr Ser Lys Leu Thr Val
865                 870                 875                 880
Asp Lys Ser Arg Trp Gln Gln Gly Asn Val Phe Ser Cys Ser Val Met
885                 890                 895
His Glu Ala Leu His Asn His Tyr Thr Gln Lys Ser Leu Ser Leu Ser
900                 905                 910
Pro Gly Lys
915

<210> SEQ ID NO 17
<211> LENGTH: 2754
<212> TYPE: DNA
<213> ORGANISM: Homo sapiens

<400> SEQUENCE: 17
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagttttga gaatacagat gctttcctgc cgttcatctc ataccccgcaa     420
atttttaacct tgtcaaccte tggggtatta gtatgccctg acctgagtga attcacccgt     480
gacaaaactg acgtgaagat tcaatggtac aaggattctc ttcttttgga taaagacaat     540
gagaaatttc taagtgtgag gggaccacct cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt     720
tcccccctca agaccatatc agcttctctg gggtcaagac tgacaatccc atgtaaggtg     780
tttctgggaa ccggcacacc cttaaccacc atgctgtggt ggacggccaa tgacaccccac     840
atagagagcg cctacccggg aggccgcgtg accgaggggc acgccaggaa atattcagaa     900
aataatgaga actacattga agtgccattg attttgatc ctgtcacaag agaggatttg     960
cacatggatt ttaaatgtgt tgtccataat accctgagtt ttcagacact acgcaccaca    1020
gtcaaggaag cctcctccac gttctcagaa cgctgcgatg actggggact agacaccatg    1080
aggcaaatcc aagtgtttga agatgagcca gctcgcatca gtgcccact ctttgaacac    1140
ttcttgaaat tcaactacag cacagcccat tcagctggcc ttactctgat ctggtattgg    1200
```

-continued

```
actaggcagg accgggacct tgaggagcca attaacttcc gcctccccga gaaccgcatt      1260
agtaaggaga aagatgtgct gtggttccgg cccactctcc tcaatgacac tggcaactat      1320
acctgcatgt taaggaacac tacatattgc agcaaagttg catttccctt ggaagttgtt      1380
caaaaagaca gctgtttcaa ttcccccatg aaactcccag tgcataaact gtatatagaa      1440
tatggcattc agaggatcac ttgtccaaat gtagatggat attttccttc cagtgtcaaa      1500
ccgactatca cttggtatat gggctgttat aaaatacaga attttaataa tgtaataccc      1560
gaaggtatga acttgagttt cctcattgcc ttaatttcaa ataatggaaa ttacacatgt      1620
gttgttacat atccagaaaa tggacgtacg tttcatctca ccaggactct gactgtaaag      1680
gtagtaggct ctccaaaaaa tgcagtgccc cctgtgatcc attcacctaa tgatcatgtg      1740
gtctatgaga agaaccagg agaggagcta ctcattccct gtacggtcta ttttagtttt       1800
ctgatggatt ctcgcaatga ggtttggtgg accattgatg aaaaaaaacc tgatgacatc      1860
actattgatg tcaccattaa cgaaagtata agtcatagta aacagaaga tgaaacaaga       1920 actcagattt tgagcatcaa gaaagttacc tctgaggatc tcaagcgcag ctatgtctgt      1980
catgctagaa gtgccaaagg cgaagttgcc aaagcagcca aggtgaagca gaaagtgcca      2040
gctccaagat acacagtgtc cggagagtcc aaatacggtc cgccatgccc atcatgccca      2100
gcacctgagt tcctgggggg accatcagtc ttcctgttcc ccccaaaacc caaggacact      2160
ctcatgatct cccggacccc tgaggtcacg tgcgtggtgg tggacgtgag ccaggaagac      2220
cccgaggtcc agttcaactg gtacgtggat ggcgtggagg tgcataatgc caagacaaag      2280
ccgcgggagg agcagttcaa cagcacgtac cgtgtggtca gcgtcctcac cgtcctgcac      2340
caggactggc tgaacggcaa ggagtacaag tgcaaggtct ccaacaaagg cctcccgtcc      2400
tccatcgaga aaaccatctc caaagccaaa gggcagcccc gagagccaca ggtgtacacc      2460
ctgcccccat cccaggagga gatgaccaag aaccaggtca gcctgacctg cctggtcaaa      2520
ggcttctacc ccagcgacat cgccgtggag tgggagagca atgggcagcc ggagaacaac      2580
tacaagacca cgcctcccgt gctggactcc gacggctcct tcttcctcta cagcaggcta      2640
accgtggaca agagcaggtg gcaggagggg aatgtcttct catgctccgt gatgcatgag      2700
gctctgcaca accactacac acagaagagc ctctccctgt ctctgggtaa atga            2754
```

<210> SEQ ID NO 18
<211> LENGTH: 917
<212> TYPE: PRT
<213> ORGANISM: Homo sapiens

<400> SEQUENCE: 18

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
        20                  25                  30

Arg His Tyr Lys Arg Glu Phe Arg Leu Glu Gly Glu Pro Val Ala Leu
    35                  40                  45

Arg Cys Pro Gln Val Pro Tyr Trp Leu Trp Ala Ser Val Ser Pro Arg
50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
        85                  90                  95

Pro Ala Leu Gln Glu Asp Ser Gly Thr Tyr Val Cys Thr Thr Arg Asn
```

```
                100             105                 110
Ala Ser Tyr Cys Asp Lys Met Ser Ile Glu Leu Arg Val Phe Glu Asn
115                 120                 125

Thr Asp Ala Phe Leu Pro Phe Ile Ser Tyr Pro Gln Ile Leu Thr Leu
130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
165                 170                 175

Asp Lys Asp Asn Glu Lys Phe Leu Ser Val Arg Gly Thr Thr His Leu
180                 185                 190

Leu Val His Asp Val Ala Leu Glu Asp Ala Gly Tyr Tyr Arg Cys Val
195                 200                 205

Leu Thr Phe Ala His Glu Gly Gln Gln Tyr Asn Ile Thr Arg Ser Ile
210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
245                 250                 255

Pro Cys Lys Val Phe Leu Gly Thr Gly Thr Pro Leu Thr Thr Met Leu
260                 265                 270

Trp Trp Thr Ala Asn Asp Thr His Ile Glu Ser Ala Tyr Pro Gly Gly
275                 280                 285

Arg Val Thr Glu Gly Pro Arg Gln Glu Tyr Ser Glu Asn Asn Glu Asn
290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
325                 330                 335

Leu Arg Thr Thr Val Lys Glu Ala Ser Ser Thr Phe Ser Glu Arg Cys
340                 345                 350

Asp Asp Trp Gly Leu Asp Thr Met Arg Gln Ile Gln Val Phe Glu Asp
355                 360                 365

Glu Pro Ala Arg Ile Lys Cys Pro Leu Phe Glu His Phe Leu Lys Phe
370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
405                 410                 415

Glu Asn Arg Ile Ser Lys Glu Lys Asp Val Leu Trp Phe Arg Pro Thr
420                 425                 430

Leu Leu Asn Asp Thr Gly Asn Tyr Thr Cys Met Leu Arg Asn Thr Thr
435                 440                 445

Tyr Cys Ser Lys Val Ala Phe Pro Leu Glu Val Val Gln Lys Asp Ser
450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
485                 490                 495

Ser Ser Val Lys Pro Thr Ile Thr Trp Tyr Met Gly Cys Tyr Lys Ile
500                 505                 510

Gln Asn Phe Asn Asn Val Ile Pro Glu Gly Met Asn Leu Ser Phe Leu
515                 520                 525
```

```
Ile Ala Leu Ile Ser Asn Asn Gly Asn Tyr Thr Cys Val Val Thr Tyr
530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
565                 570                 575

Asn Asp His Val Val Tyr Glu Lys Glu Pro Gly Glu Leu Leu Ile
580                 585                 590

Pro Cys Thr Val Tyr Phe Ser Phe Leu Met Asp Ser Arg Asn Glu Val
595                 600                 605

Trp Trp Thr Ile Asp Gly Lys Lys Pro Asp Asp Ile Thr Ile Asp Val
610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
645                 650                 655

Ser Tyr Val Cys His Ala Arg Ser Ala Lys Gly Glu Val Ala Lys Ala
660                 665                 670

Ala Lys Val Lys Gln Lys Val Pro Ala Pro Arg Tyr Thr Val Ser Gly
675                 680                 685

Glu Ser Lys Tyr Gly Pro Pro Cys Pro Ser Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
725                 730                 735

Ser Gln Glu Asp Pro Glu Val Gln Phe Asn Trp Tyr Val Asp Gly Val
740                 745                 750

Glu Val His Asn Ala Lys Thr Lys Pro Arg Glu Glu Gln Phe Asn Ser
755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
805                 810                 815

Gln Val Tyr Thr Leu Pro Pro Ser Gln Glu Glu Met Thr Lys Asn Gln
820                 825                 830

Val Ser Leu Thr Cys Leu Val Lys Gly Phe Tyr Pro Ser Asp Ile Ala
835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
885                 890                 895

Val Met His Glu Ala Leu His Asn His Tyr Thr Gln Lys Ser Leu Ser
900                 905                 910

Leu Ser Leu Gly Lys
915

<210> SEQ ID NO 19
<211> LENGTH: 2754
```

<212> TYPE: DNA
<213> ORGANISM: Homo sapiens

<400> SEQUENCE: 19

```
atggtgcgct tgtacgtgtt ggtaatggga gtttctgcct tcacccttca gcctgcggca      60
cacacagggg ctgccagaag ctgccggttt cgtgggaggc attacaagcg ggagttcagg     120
ctggaagggg agcctgtagc cctgaggtgc cccaggtgc cctactggtt gtgggcctct      180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagttttga gaatacagat gctttcctgc cgttcatctc atacccgcaa      420
attttaacct tgtcaacctc tggggtatta gtatgccctg acctgagtga attcacccgt     480
gacaaaactg acgtgaagat tcaatggtac aaggattctc ttcttttgga taaagacaat     540
gagaaatttc taagtgtgag ggggaccact cacttactcg tacacgatgt ggccctggaa     600
gatgctggct attaccgctg tgtcctgaca tttgcccatg aaggccagca atacaacatc     660
actaggagta ttgagctacg catcaagaaa aaaaagaag agaccattcc tgtgatcatt      720
tccccctca agaccatatc agcttctctg gggtcaagac tgacaatccc atgtaaggtg      780
tttctgggaa ccggcacacc cttaaccacc atgctgtggt ggacggccaa tgacacccac     840
atagagagcg cctacccggg aggccgcgtg accgaggggc cacgccagga atattcagaa     900
aataatgaga actacattga agtgccattg attttgatc ctgtcacaag agaggatttg      960
cacatggatt ttaaatgtgt tgtccataat accctgagtt ttcagacact acgcaccaca    1020
gtcaaggaag cctcctccac gttctcagaa cgctgcgatg actggggact agacaccatg    1080
aggcaaatcc aagtgtttga agatgagcca gctcgcatca gtgcccact ctttgaacac     1140
ttcttgaaat tcaactacag cacagcccat tcagctggcc ttactctgat ctggtattgg    1200
actaggcagg accgggacct tgaggagcca attaacttcc gcctccccga gaaccgcatt    1260
agtaaggaga aagatgtgct gtggttccgg cccactctcc tcaatgacac tggcaactat    1320
acctgcatgt taaggaacac tacatattgc agcaaagttg catttcccctt ggaagttgtt   1380
caaaaagaca gctgtttcaa ttcccccatg aaactcccag tgcataaact gtatatagaa    1440
tatggcattc agaggatcac ttgtccaaat gtagatggat atttttcttc cagtgtcaaa    1500
ccgactatca cttggtatat gggctgttat aaaatacaga attttaataa tgtaataccc    1560
gaaggtatga acttgagttt cctcattgcc ttaatttcaa ataatggaaa ttacacatgt    1620
gttgttacat atcagaaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga aagaaccagg agaggagcta ctcattccct gtacggtcta ttttagtttt    1800
ctgatggatt ctcgcaatga ggtttggtgg accattgatg aaaaaaacc tgatgacatc     1860
actattgatg tcaccattaa cgaaagtata agtcatagta aacagaaga tgaaacaaga    1920
actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagagtcc aaatacggtc cgccatgccc accatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
```

-continued

```
cccgaggtcc agttcaactg gtacgtggat ggcgtggagg tgcataatgc caagacaaag    2280
ccgcgggagg agcagttcaa cagcacgtac cgtgtggtca cgtcctcac cgtcctgcac     2340 caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca tgggcagcc ggagaacaac     2580 tacaagacca cgcctcccgt gctggactcc gacggctcct tcttcctcta cagcaggcta    2640
accgtggaca gagcaggtg gcaggagggg aatgtcttct catgctccgt gatgcatgag     2700
gctctgcaca accactacac acagaagagc ctctccctgt ctctgggtaa atga          2754
```

<210> SEQ ID NO 20
<211> LENGTH: 917
<212> TYPE: PRT
<213> ORGANISM: Homo sapiens

<400> SEQUENCE: 20

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Pro Val Ala Leu
35                  40                  45

Arg Cys Pro Gln Val Pro Tyr Trp Leu Trp Ala Ser Val Ser Pro Arg
50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285
```

-continued

```
Arg Val Thr Glu Gly Pro Arg Gln Glu Tyr Ser Glu Asn Asn Glu Asn
290                 295                 300
Tyr Ile Glu Val Pro Leu Ile Phe Asp Pro Val Thr Arg Glu Asp Leu
305                 310                 315                 320
His Met Asp Phe Lys Cys Val Val His Asn Thr Leu Ser Phe Gln Thr
325                 330                 335
Leu Arg Thr Thr Val Lys Glu Ala Ser Ser Thr Phe Ser Glu Arg Cys
340                 345                 350
Asp Asp Trp Gly Leu Asp Thr Met Arg Gln Ile Gln Val Phe Glu Asp
355                 360                 365
Glu Pro Ala Arg Ile Lys Cys Pro Leu Phe Glu His Phe Leu Lys Phe
370                 375                 380
Asn Tyr Ser Thr Ala His Ser Ala Gly Leu Thr Leu Ile Trp Tyr Trp
385                 390                 395                 400
Thr Arg Gln Asp Arg Asp Leu Glu Glu Pro Ile Asn Phe Arg Leu Pro
405                 410                 415
Glu Asn Arg Ile Ser Lys Glu Lys Asp Val Leu Trp Phe Arg Pro Thr
420                 425                 430
Leu Leu Asn Asp Thr Gly Asn Tyr Thr Cys Met Leu Arg Asn Thr Thr
435                 440                 445
Tyr Cys Ser Lys Val Ala Phe Pro Leu Glu Val Val Gln Lys Asp Ser
450                 455                 460
Cys Phe Asn Ser Pro Met Lys Leu Pro Val His Lys Leu Tyr Ile Glu
465                 470                 475                 480
Tyr Gly Ile Gln Arg Ile Thr Cys Pro Asn Val Asp Gly Tyr Phe Pro
485                 490                 495
Ser Ser Val Lys Pro Thr Ile Thr Trp Tyr Met Gly Cys Tyr Lys Ile
500                 505                 510
Gln Asn Phe Asn Asn Val Ile Pro Glu Gly Met Asn Leu Ser Phe Leu
515                 520                 525
Ile Ala Leu Ile Ser Asn Asn Gly Asn Tyr Thr Cys Val Val Thr Tyr
530                 535                 540
Pro Glu Asn Gly Arg Thr Phe His Leu Thr Arg Thr Leu Thr Val Lys
545                 550                 555                 560
Val Val Gly Ser Pro Lys Asn Ala Val Pro Pro Val Ile His Ser Pro
565                 570                 575
Asn Asp His Val Val Tyr Glu Lys Glu Pro Gly Glu Glu Leu Leu Ile
580                 585                 590
Pro Cys Thr Val Tyr Phe Ser Phe Leu Met Asp Ser Arg Asn Glu Val
595                 600                 605
Trp Trp Thr Ile Asp Gly Lys Lys Pro Asp Asp Ile Thr Ile Asp Val
610                 615                 620
Thr Ile Asn Glu Ser Ile Ser His Ser Arg Thr Glu Asp Glu Thr Arg
625                 630                 635                 640
Thr Gln Ile Leu Ser Ile Lys Lys Val Thr Ser Glu Asp Leu Lys Arg
645                 650                 655
Ser Tyr Val Cys His Ala Arg Ser Ala Lys Gly Glu Val Ala Lys Ala
660                 665                 670
Ala Lys Val Lys Gln Lys Val Pro Ala Pro Arg Tyr Thr Val Ser Gly
675                 680                 685
Glu Ser Lys Tyr Gly Pro Pro Cys Pro Pro Cys Pro Ala Pro Glu Phe
690                 695                 700
```

```
Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
            725                 730                 735

Ser Gln Glu Asp Pro Glu Val Gln Phe Asn Trp Tyr Val Asp Gly Val
740                 745                 750

Glu Val His Asn Ala Lys Thr Lys Pro Arg Glu Glu Gln Phe Asn Ser
755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
805                 810                 815

Gln Val Tyr Thr Leu Pro Pro Ser Gln Glu Glu Met Thr Lys Asn Gln
820                 825                 830

Val Ser Leu Thr Cys Leu Val Lys Gly Phe Tyr Pro Ser Asp Ile Ala
835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
885                 890                 895

Val Met His Glu Ala Leu His Asn His Tyr Thr Gln Lys Ser Leu Ser
900                 905                 910

Leu Ser Leu Gly Lys
915

<210> SEQ ID NO 21
<211> LENGTH: 2748
<212> TYPE: DNA
<213> ORGANISM: Homo sapiens

<400> SEQUENCE: 21
atggtgcttc tgtggtgtgt agtgagtctc tacttttatg gaatcctgca aagtgatgcc      60
tcagaacgct gcgatgactg gggactagac accatgaggc aaatccaagt gtttgaagat    120
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactataccc tgcatgttaa gaacactaca    360
tattgcagca agttgcatt tcccttggaa gttgttcaaa agacagctg tttcaattcc    420 cccatgaaac tcccagtgca taactgtat atagaatatg cattcagag atcacttgt    480 ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720 gtgcccctg tgatccattc acctaatgat catgtggtct atgagaaaga accaggagag    780
gagctactca ttcctgtac ggtctatttt agttttctga tggattctcg caatgaggtt    840
tggtggacca ttgatggaaa aaacctgat gacatcacta ttgatgtcac cattaacgaa    900
```

```
agtataagtc atagtagaac agaagatgaa acaagaactc agattttgag catcaagaaa        960
gttacctctg aggatctcaa gcgcagctat gtctgtcatg ctagaagtgc caaaggcgaa       1020
gttgccaaag cagccaaggt gaagcagaaa gtgccagctc aagatacac agtgcacaca        1080
ggggctgcca gaagctgccg gtttcgtggg aggcattaca agcgggagtt caggctggaa       1140
ggggagcctg tagccctgag gtgccccag gtgccctact ggttgtgggc ctctgtcagc        1200
ccccgcatca acctgacatg gcataaaaat gactctgcta ggacggtccc aggagaagaa       1260
gagacacgga tgtgggccca ggacggtgct ctgtggcttc tgccagcctt gcaggaggac       1320
tctggcacct acgtctgcac tactagaaat gcttcttact gtgacaaaat gtccattgag       1380
ctcagagttt ttgagaatac agatgctttc ctgccgttca tctcataccc gcaaatttta       1440
accttgtcaa cctctggggt attagtatgc cctgacctga gtgaattcac ccgtgacaaa       1500
actgacgtga agattcaatg gtacaaggat tctcttcttt tggataaaga caatgagaaa       1560
tttctaagtg tgaggggga cactcactta ctcgtacacg atgtggccct ggaagatgct        1620
ggctattacc gctgtgtcct gacatttgcc catgaaggcc agcaatacaa catcactagg       1680
agtattgagc tacgcatcaa gaaaaaaaaa gaagagacca ttcctgtgat catttccccc       1740
ctcaagacca tatcagcttc tctggggtca agactgacaa tcccatgtaa ggtgtttctg       1800
ggaaccggca cacccttaac caccatgctg tggtggacgg ccaatgacac ccacatagag       1860
agcgcctacc cggaggccg cgtgaccgag gggccacgcc aggaatattc agaaaataat        1920
gagaactaca ttgaagtgcc attgattttt gatcctgtca agagagga tttgcacatg         1980
gattttaaat gtgttgtcca taatacccctg agttttcaga cactacgcac cacagtcaag      2040
gaagcctcct ccacgttctc cggagacaaa actcacacat gcccaccgtg cccagcacct      2100
gaactcctgg ggggaccgtc agtcttcctc ttcccccccaa aacccaagga caccctcatg      2160
atctcccgga cccctgaggt cacatgcgtg gtggtggacg tgagccacga agaccctgag      2220
gtcaagttca actggtacgt ggacggcgtg gaggtgcata atgccaagac aaagccgcgg      2280
gaggagcagt acaacagcac gtaccgtgtg gtcagcgtcc tcaccgtcct gcaccaggac      2340
tggctgaatg gcaaggagta caagtgcaag gtctccaaca aagccctccc agcccccatc      2400
gagaaaacca tctccaaagc caaagggcag ccccgagaac acaggtgta cacctgccc       2460
ccatcccggg atgagctgac caagaaccag gtcagcctga cctgcctggt caaaggcttc      2520
tatcccagcg acatcgccgt ggagtgggag agcaatgggc agccggagaa caactacaag      2580
accacgcctc ccgtgctgga ctccgacggc tccttcttcc tctatagcaa gctcaccgtg      2640
gacaagagca ggtggcagca ggggaacgtc ttctcatgct ccgtgatgca tgaggctctg      2700
cacaaccact acacgcagaa gagcctctcc ctgtctccgg gtaaatga                   2748
```

<210> SEQ ID NO 22
<211> LENGTH: 915
<212> TYPE: PRT
<213> ORGANISM: Homo sapiens

<400> SEQUENCE: 22

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
        20                  25                  30

Arg Gln Ile Gln Val Phe Glu Asp Glu Pro Ala Arg Ile Lys Cys Pro
    35                  40                  45

```
Leu Phe Glu His Phe Leu Lys Phe Asn Tyr Ser Thr Ala His Ser Ala
 50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
 85                  90                  95

Asp Val Leu Trp Phe Arg Pro Thr Leu Leu Asn Asp Thr Gly Asn Tyr
100                 105                 110

Thr Cys Met Leu Arg Asn Thr Thr Tyr Cys Ser Lys Val Ala Phe Pro
115                 120                 125

Leu Glu Val Val Gln Lys Asp Ser Cys Phe Asn Ser Pro Met Lys Leu
130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
165                 170                 175

Trp Tyr Met Gly Cys Tyr Lys Ile Gln Asn Phe Asn Asn Val Ile Pro
180                 185                 190

Glu Gly Met Asn Leu Ser Phe Leu Ile Ala Leu Ile Ser Asn Asn Gly
195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
245                 250                 255

Glu Pro Gly Glu Glu Leu Leu Ile Pro Cys Thr Val Tyr Phe Ser Phe
260                 265                 270

Leu Met Asp Ser Arg Asn Glu Val Trp Trp Thr Ile Asp Gly Lys Lys
275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
325                 330                 335

Ala Lys Gly Glu Val Ala Lys Ala Ala Lys Val Lys Gln Lys Val Pro
340                 345                 350

Ala Pro Arg Tyr Thr Val His Thr Gly Ala Ala Arg Ser Cys Arg Phe
355                 360                 365

Arg Gly Arg His Tyr Lys Arg Glu Phe Arg Leu Glu Gly Glu Pro Val
370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
405                 410                 415

Pro Gly Glu Glu Glu Thr Arg Met Trp Ala Gln Asp Gly Ala Leu Trp
420                 425                 430

Leu Leu Pro Ala Leu Gln Glu Asp Ser Gly Thr Tyr Val Cys Thr Thr
435                 440                 445

Arg Asn Ala Ser Tyr Cys Asp Lys Met Ser Ile Glu Leu Arg Val Phe
450                 455                 460
```

-continued

```
Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
485                 490                 495

Thr Arg Asp Lys Thr Asp Val Lys Ile Gln Trp Tyr Lys Asp Ser Leu
500                 505                 510

Leu Leu Asp Lys Asp Asn Glu Lys Phe Leu Ser Val Arg Gly Thr Thr
515                 520                 525

His Leu Leu Val His Asp Val Ala Leu Glu Asp Ala Gly Tyr Tyr Arg
530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
565                 570                 575

Ile Ile Ser Pro Leu Lys Thr Ile Ser Ala Ser Leu Gly Ser Arg Leu
580                 585                 590

Thr Ile Pro Cys Lys Val Phe Leu Gly Thr Gly Thr Pro Leu Thr Thr
595                 600                 605

Met Leu Trp Trp Thr Ala Asn Asp Thr His Ile Glu Ser Ala Tyr Pro
610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
645                 650                 655

Asp Leu His Met Asp Phe Lys Cys Val Val His Asn Thr Leu Ser Phe
660                 665                 670

Gln Thr Leu Arg Thr Thr Val Lys Glu Ala Ser Ser Thr Phe Ser Gly
675                 680                 685

Asp Lys Thr His Thr Cys Pro Pro Cys Pro Ala Pro Glu Leu Leu Gly
690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
725                 730                 735

Glu Asp Pro Glu Val Lys Phe Asn Trp Tyr Val Asp Gly Val Glu Val
740                 745                 750

His Asn Ala Lys Thr Lys Pro Arg Glu Glu Gln Tyr Asn Ser Thr Tyr
755                 760                 765

Arg Val Val Ser Val Leu Thr Val Leu His Gln Asp Trp Leu Asn Gly
770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
805                 810                 815

Tyr Thr Leu Pro Pro Ser Arg Asp Glu Leu Thr Lys Asn Gln Val Ser
820                 825                 830

Leu Thr Cys Leu Val Lys Gly Phe Tyr Pro Ser Asp Ile Ala Val Glu
835                 840                 845

Trp Glu Ser Asn Gly Gln Pro Glu Asn Asn Tyr Lys Thr Thr Pro Pro
850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
```

His Glu Ala Leu His Asn His Tyr Thr Gln Lys Ser Leu Ser Leu Ser
　　　　　　　　　900　　　　　　　　　　　905　　　　　　　　　910

Pro Gly Lys
915

<210> SEQ ID NO 23
<211> LENGTH: 2754
<212> TYPE: DNA
<213> ORGANISM: Homo sapiens

<400> SEQUENCE: 23

| | | | | | |
|---|---|---|---|---|---|
| atggtgcttc | tgtggtgtgt | agtgagtctc | tacttttatg | gaatcctgca | aagtgatgcc    60 |
| tcagaacgct | gcgatgactg | gggactagac | accatgaggc | aaatccaagt | gtttgaagat   120 |
| gagccagctc | gcatcaagtg | cccactcttt | gaacacttct | tgaaattcaa | ctacagcaca   180 |
| gcccattcag | ctggccttac | tctgatctgg | tattggacta | gcaggaccg | ggaccttgag   240 |
| gagccaatta | acttccgcct | ccccgagaac | cgcattagta | aggagaaaga | tgtgctgtgg   300 |
| ttccggccca | ctctcctcaa | tgacactggc | aactatacct | gcatgttaag | gaacactaca   360 |
| tattgcagca | agttgcatt | tcccttggaa | gttgttcaaa | aagacagctg | tttcaattcc   420 |
| cccatgaaac | tcccagtgca | taaactgtat | atagaatatg | gcattcagag | gatcacttgt   480 |
| ccaaatgtag | atggatattt | tccttccagt | gtcaaaccga | ctatcacttg | gtatatgggc   540 |
| tgttataaaa | tacagaattt | taataatgta | atacccgaag | gtatgaactt | gagtttcctc   600 |
| attgccttaa | tttcaaataa | tggaaattac | acatgtgttg | ttacatatcc | agaaaatgga   660 |
| cgtacgtttc | atctcaccag | gactctgact | gtaaaggtag | taggctctcc | aaaaaatgca   720 |
| gtgccccctg | tgatccattc | acctaatgat | catgtggtct | atgagaaaga | accaggagag   780 |
| gagctactca | ttccctgtac | ggtctatttt | agttttctga | tggattctcg | caatgaggtt   840 |
| tggtggacca | ttgatggaaa | aaaacctgat | gacatcacta | ttgatgtcac | cattaacgaa   900 |
| agtataagtc | atagtagaac | agaagatgaa | acaagaactc | agatttttgag | catcaagaaa   960 |
| gttacctctg | aggatctcaa | gcgcagctat | gtctgtcatg | ctagaagtgc | caaaggcgaa  1020 |
| gttgccaaag | cagccaaggt | gaagcagaaa | gtgccagctc | aagatacac | agtgcacaca  1080 |
| ggggctgcca | gaagctgccg | gttcgtgggg | aggcattaca | agcgggagtt | caggctggaa  1140 |
| ggggagcctg | tagccctgag | gtgccccag | gtgccctact | ggttgtgggc | ctctgtcagc  1200 |
| ccccgcatca | acctgacatg | gcataaaaat | gactctgcta | ggacggtccc | aggagaagaa  1260 |
| gagacacgga | tgtgggccca | ggacggtgct | ctgtggcttc | tgccagcctt | gcaggaggac  1320 |
| tctggcacct | acgtctgcac | tactagaaat | gcttcttact | gtgacaaaat | gtccattgag  1380 |
| ctcagagttt | ttgagaatac | agatgctttc | ctgccgttca | tctcataccc | gcaaattta   1440 |
| accttgtcaa | cctctggggt | attagtatgc | cctgacctga | gtgaattcac | ccgtgacaaa  1500 |
| actgacgtga | agattcaatg | gtacaaggat | tctcttcttt | tggataaaga | caatgagaaa  1560 |
| tttctaagtg | tgagggggac | cactcactta | ctcgtacacg | atgtggccct | ggaagatgct  1620 |
| ggctattacc | gctgtgtcct | gacatttgcc | catgaaggcc | agcaatacaa | catcactagg  1680 |
| agtattgagc | tacgcatcaa | gaaaaaaaa | gaagagacca | ttcctgtgat | catttccccc  1740 |
| ctcaagacca | tatcagcttc | tctggggtca | agactgacaa | tcccatgtaa | ggtgttctg   1800 |
| ggaaccggca | cacccttaac | caccatgctg | tggtggacgg | ccaatgacac | ccacatagag  1860 |
| agcgcctacc | cgggaggccg | cgtgaccgag | gggccacgcc | aggaatattc | agaaaataat  1920 |

-continued

```
gagaactaca ttgaagtgcc attgattttt gatcctgtca caagagagga tttgcacatg   1980
gattttaaat gtgttgtcca taatacctg agttttcaga cactacgcac cacagtcaag    2040
gaagcctcct ccacgttctc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca agagcaggtg gcaggagggg aatgtcttct catgctccgt gatgcatgag   2700
gctctgcaca accactacac acagaagagc ctctccctgt ctctgggtaa atga         2754
```

<210> SEQ ID NO 24
<211> LENGTH: 917
<212> TYPE: PRT
<213> ORGANISM: Homo sapiens

<400> SEQUENCE: 24

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220
```

```
Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
            245                 250                 255

Glu Pro Gly Glu Glu Leu Leu Ile Pro Cys Thr Val Tyr Phe Ser Phe
260                 265                 270

Leu Met Asp Ser Arg Asn Glu Val Trp Trp Thr Ile Asp Gly Lys Lys
275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
325                 330                 335

Ala Lys Gly Glu Val Ala Lys Ala Ala Lys Val Lys Gln Lys Val Pro
340                 345                 350

Ala Pro Arg Tyr Thr Val His Thr Gly Ala Ala Arg Ser Cys Arg Phe
355                 360                 365

Arg Gly Arg His Tyr Lys Arg Glu Phe Arg Leu Glu Gly Glu Pro Val
370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
405                 410                 415

Pro Gly Glu Glu Glu Thr Arg Met Trp Ala Gln Asp Gly Ala Leu Trp
420                 425                 430

Leu Leu Pro Ala Leu Gln Glu Asp Ser Gly Thr Tyr Val Cys Thr Thr
435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
485                 490                 495

Thr Arg Asp Lys Thr Asp Val Lys Ile Gln Trp Tyr Lys Asp Ser Leu
500                 505                 510

Leu Leu Asp Lys Asp Asn Glu Lys Phe Leu Ser Val Arg Gly Thr Thr
515                 520                 525

His Leu Leu Val His Asp Val Ala Leu Glu Asp Ala Gly Tyr Tyr Arg
530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
565                 570                 575

Ile Ile Ser Pro Leu Lys Thr Ile Ser Ala Ser Leu Gly Ser Arg Leu
580                 585                 590

Thr Ile Pro Cys Lys Val Phe Leu Gly Thr Gly Thr Pro Leu Thr Thr
595                 600                 605

Met Leu Trp Trp Thr Ala Asn Asp Thr His Ile Glu Ser Ala Tyr Pro
610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
```

-continued

```
            645                 650                 655
Asp Leu His Met Asp Phe Lys Cys Val Val His Asn Thr Leu Ser Phe
660                 665                 670

Gln Thr Leu Arg Thr Thr Val Lys Glu Ala Ser Ser Thr Phe Ser Gly
675                 680                 685

Glu Ser Lys Tyr Gly Pro Pro Cys Pro Ser Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
725                 730                 735

Ser Gln Glu Asp Pro Glu Val Gln Phe Asn Trp Tyr Val Asp Gly Val
740                 745                 750

Glu Val His Asn Ala Lys Thr Lys Pro Arg Glu Glu Gln Phe Asn Ser
755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
805                 810                 815

Gln Val Tyr Thr Leu Pro Pro Ser Gln Glu Glu Met Thr Lys Asn Gln
820                 825                 830

Val Ser Leu Thr Cys Leu Val Lys Gly Phe Tyr Pro Ser Asp Ile Ala
835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
885                 890                 895

Val Met His Glu Ala Leu His Asn His Tyr Thr Gln Lys Ser Leu Ser
900                 905                 910

Leu Ser Leu Gly Lys
915

<210> SEQ ID NO 25
<211> LENGTH: 2754
<212> TYPE: DNA
<213> ORGANISM: Homo sapiens

<400> SEQUENCE: 25
atggtgcttc tgtggtgtgt agtgagtctc tactttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca    180
gcccattcag ctggccttac tctgatctgg tattggacta gcaggaccg ggaccttgag     240 gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa agacagctg tttcaattcc    420 cccatgaaac tcccagtgca taactgtat atagaatatg gcattcagag gatcacttgt    480
ccaaatgtag atggatattt tccttccagt gtcaaaccga ctatcacttg gtatatgggc    540
```

```
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgcccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc aagatacac agtgcacaca   1080
ggggctgcca gaagctgccg gtttcgtggg aggcattaca agcgggagtt caggctggaa   1140
ggggagcctg tagccctgag gtgccccag gtgccctact ggttgtgggc ctctgtcagc   1200
ccccgcatca acctgacatg gcataaaaat gactctgcta ggacggtccc aggagaagaa   1260
gagacacgga tgtgggccca ggacggtgct ctgtggcttc tgccagcctt gcaggaggac   1320
tctggcacct acgtctgcac tactagaaat gcttcttact gtgacaaaat gtccattgag   1380
ctcagagttt ttgagaatac agatgctttc ctgccgttca tctcataccc gcaaatttta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgaggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca cacccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca caagagagga tttgcacatg   1980
gattttaaat gtgttgtcca taatccctg agttttcaga cactacgcac cacagtcaag   2040
gaagcctcct ccacgttctc cggagagtcc aaatacggtc cgccatgccc accatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagt gcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca gagcaggtg gcaggagggg aatgtcttct catgctccgt gatgcatgag   2700
gctctgcaca accactacac acagaagagc ctctccctgt ctctgggtaa atga          2754
```

<210> SEQ ID NO 26
<211> LENGTH: 917
<212> TYPE: PRT
<213> ORGANISM: Homo sapiens

<400> SEQUENCE: 26

```
Met Val Leu Leu Trp Cys Val Val Ser Leu Tyr Phe Tyr Gly Ile Leu
1               5                   10                  15
Gln Ser Asp Ala Ser Glu Arg Cys Asp Asp Trp Gly Leu Asp Thr Met
            20                  25                  30
Arg Gln Ile Gln Val Phe Glu Asp Glu Pro Ala Arg Ile Lys Cys Pro
35                  40                  45
Leu Phe Glu His Phe Leu Lys Phe Asn Tyr Ser Thr Ala His Ser Ala
50                  55                  60
Gly Leu Thr Leu Ile Trp Tyr Trp Thr Arg Gln Asp Arg Asp Leu Glu
65                  70                  75                  80
Glu Pro Ile Asn Phe Arg Leu Pro Glu Asn Arg Ile Ser Lys Glu Lys
                85                  90                  95
Asp Val Leu Trp Phe Arg Pro Thr Leu Leu Asn Asp Thr Gly Asn Tyr
            100                 105                 110
Thr Cys Met Leu Arg Asn Thr Thr Tyr Cys Ser Lys Val Ala Phe Pro
115                 120                 125
Leu Glu Val Val Gln Lys Asp Ser Cys Phe Asn Ser Pro Met Lys Leu
130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
            180                 185                 190
Glu Gly Met Asn Leu Ser Phe Leu Ile Ala Leu Ile Ser Asn Asn Gly
195                 200                 205
Asn Tyr Thr Cys Val Val Thr Tyr Pro Glu Asn Gly Arg Thr Phe His
210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
            260                 265                 270
Leu Met Asp Ser Arg Asn Glu Val Trp Trp Thr Ile Asp Gly Lys Lys
275                 280                 285
Pro Asp Asp Ile Thr Ile Asp Val Thr Ile Asn Glu Ser Ile Ser His
290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
            340                 345                 350
Ala Pro Arg Tyr Thr Val His Thr Gly Ala Ala Arg Ser Cys Arg Phe
355                 360                 365
Arg Gly Arg His Tyr Lys Arg Glu Phe Arg Leu Glu Gly Glu Pro Val
370                 375                 380
Ala Leu Arg Cys Pro Gln Val Pro Tyr Trp Leu Trp Ala Ser Val Ser
385                 390                 395                 400
Pro Arg Ile Asn Leu Thr Trp His Lys Asn Asp Ser Ala Arg Thr Val
```

```
                            405                 410                 415
Pro Gly Glu Glu Thr Arg Met Trp Ala Gln Asp Gly Ala Leu Trp
420                 425                 430

Leu Leu Pro Ala Leu Gln Glu Asp Ser Gly Thr Tyr Val Cys Thr Thr
435                 440                 445

Arg Asn Ala Ser Tyr Cys Asp Lys Met Ser Ile Glu Leu Arg Val Phe
450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
485                 490                 495

Thr Arg Asp Lys Thr Asp Val Lys Ile Gln Trp Tyr Lys Asp Ser Leu
500                 505                 510

Leu Leu Asp Lys Asp Asn Glu Lys Phe Leu Ser Val Arg Gly Thr Thr
515                 520                 525

His Leu Leu Val His Asp Val Ala Leu Glu Asp Ala Gly Tyr Tyr Arg
530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
565                 570                 575

Ile Ile Ser Pro Leu Lys Thr Ile Ser Ala Ser Leu Gly Ser Arg Leu
580                 585                 590

Thr Ile Pro Cys Lys Val Phe Leu Gly Thr Gly Thr Pro Leu Thr Thr
595                 600                 605

Met Leu Trp Trp Thr Ala Asn Asp Thr His Ile Glu Ser Ala Tyr Pro
610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
645                 650                 655

Asp Leu His Met Asp Phe Lys Cys Val Val His Asn Thr Leu Ser Phe
660                 665                 670

Gln Thr Leu Arg Thr Thr Val Lys Glu Ala Ser Ser Thr Phe Ser Gly
675                 680                 685

Glu Ser Lys Tyr Gly Pro Pro Cys Pro Pro Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
725                 730                 735

Ser Gln Glu Asp Pro Glu Val Gln Phe Asn Trp Tyr Val Asp Gly Val
740                 745                 750

Glu Val His Asn Ala Lys Thr Lys Pro Arg Glu Gln Phe Asn Ser
755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
805                 810                 815

Gln Val Tyr Thr Leu Pro Pro Ser Gln Glu Glu Met Thr Lys Asn Gln
820                 825                 830
```

-continued

```
Val Ser Leu Thr Cys Leu Val Lys Gly Phe Tyr Pro Ser Asp Ile Ala
835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
885                 890                 895

Val Met His Glu Ala Leu His Asn His Tyr Thr Gln Lys Ser Leu Ser
900                 905                 910

Leu Ser Leu Gly Lys
915
```